(12) United States Patent
Menear et al.

(10) Patent No.: US 8,247,416 B2
(45) Date of Patent: Aug. 21, 2012

(54) PHTHALAZINONE DERIVATIVE

(75) Inventors: Keith Allan Menear, Cambridge (GB); Anthony Peter Ottridge, Cambridge (GB); Derek John Londesbrough, Sunderland (GB); Michael Raymond Hallett, Sunderland (GB); Keith Raymond Mulholland, Macclesfield (GB); John David Pittam, Macclesfield (GB); David Dermot Patrick Laffan, Macclesfield (GB); Ian Woodward Ashworth, Macclesfield (GB); Martin Francis Jones, Macclesfield (GB); Janette Helen Cherryman, Macclesfield (GB)

(73) Assignee: Kudos Pharmaceuticals Limited, London (GB)

( * ) Notice: Subject to any disclaimer, the term of this patent is extended or adjusted under 35 U.S.C. 154(b) by 343 days.

(21) Appl. No.: 12/500,900

(22) Filed: Jul. 10, 2009

(65) Prior Publication Data

US 2009/0270617 A1 Oct. 29, 2009

Related U.S. Application Data

(63) Continuation of application No. 11/873,671, filed on Oct. 17, 2007, now Pat. No. 7,692,006.

(60) Provisional application No. 60/829,694, filed on Oct. 17, 2006.

(51) Int. Cl.
*A01N 43/58* (2006.01)
*A61K 31/50* (2006.01)
(52) U.S. Cl. .......... 514/248; 544/237; 549/307
(58) Field of Classification Search .................. 544/237; 549/307; 514/248
See application file for complete search history.

(56) References Cited

U.S. PATENT DOCUMENTS

| | | | |
|---|---|---|---|
| 3,813,384 A | 5/1974 | Vogelsang et al. |
| 4,665,181 A | 5/1987 | Thomas et al. |
| 4,841,047 A | 6/1989 | Engel et al. |
| 5,032,617 A | 7/1991 | Lee et al. |
| 5,041,653 A | 8/1991 | Lee et al. |
| 5,215,738 A | 6/1993 | Lee et al. |
| 5,556,856 A | 9/1996 | Engel et al. |
| 5,587,384 A | 12/1996 | Zhang et al. |
| 5,648,355 A | 7/1997 | Theoharides |
| 5,817,674 A | 10/1998 | Clemence et al. |
| 5,854,264 A | 12/1998 | Anthony et al. |
| 5,854,265 A | 12/1998 | Anthony |
| 5,859,035 A | 1/1999 | Anthony et al. |
| 5,872,136 A | 2/1999 | Anthony et al. |
| 5,874,444 A | 2/1999 | West |
| 5,874,452 A | 2/1999 | Anthony |
| 5,880,128 A | 3/1999 | Doll et al. |
| 5,880,140 A | 3/1999 | Anthony |
| 5,883,105 A | 3/1999 | Anthony |
| 5,939,557 A | 8/1999 | Anthony et al. |
| 6,004,979 A | 12/1999 | Clemence et al. |
| 6,011,035 A | 1/2000 | Snutch et al. |
| 6,051,574 A | 4/2000 | Anthony |
| 6,060,038 A | 5/2000 | Burns et al. |
| 6,063,930 A | 5/2000 | Dinsmore et al. |
| 6,080,870 A | 6/2000 | Anthony et al. |
| 6,197,785 B1 | 3/2001 | Jackson et al. |
| 6,294,533 B1 | 9/2001 | Snutch et al. |
| 6,310,059 B1 | 10/2001 | Snutch |
| 6,387,897 B1 | 5/2002 | Snutch |
| 6,426,415 B1 | 7/2002 | Jackson et al. |
| 6,465,467 B1 | 10/2002 | Nilsson et al. |
| 6,476,048 B1 | 11/2002 | Szabo et al. |
| 6,492,375 B2 | 12/2002 | Snutch |
| 6,514,984 B1 | 2/2003 | Watanabe |
| 6,552,016 B1 | 4/2003 | Baxter et al. |
| 6,617,322 B2 | 9/2003 | Snutch |
| 6,635,642 B1 | 10/2003 | Jackson et al. |
| 6,891,041 B2 | 5/2005 | Petrov et al. |
| 6,943,168 B2 | 9/2005 | Snutch et al. |
| 6,949,554 B2 | 9/2005 | Snutch et al. |
| 6,951,862 B2 | 10/2005 | Snutch et al. |
| 6,953,857 B2 | 10/2005 | Nazaré et al. |
| 7,064,128 B2 | 6/2006 | Snutch et al. |
| 7,067,665 B2 | 6/2006 | Nazare et al. |
| 7,071,180 B2 | 7/2006 | Nilsson et al. |
| 7,151,102 B2 | 12/2006 | Martin et al. |
| 7,186,726 B2 | 3/2007 | Snutch et al. |
| 7,196,085 B2 | 3/2007 | Martin et al. |
| 7,407,957 B2 | 8/2008 | Javaid et al. |
| 2001/0029258 A1 | 10/2001 | Snutch |
| 2003/0022819 A1 | 1/2003 | Ling et al. |
| 2003/0045530 A1 | 3/2003 | Snutch |
| 2003/0092694 A1 | 5/2003 | Nilsson et al. |
| 2003/0195192 A1 | 10/2003 | Haviv et al. |
| 2003/0195195 A1 | 10/2003 | Haviv et al. |
| 2004/0014744 A1 | 1/2004 | Haviv et al. |
| 2004/0023949 A1 | 2/2004 | Baxter et al. |
| 2004/0034035 A1 | 2/2004 | Snutch et al. |

(Continued)

FOREIGN PATENT DOCUMENTS

EP 0355750 2/1990

(Continued)

OTHER PUBLICATIONS

United States Patent Office Action for U.S. Appl. No. 10/021,506 dated Nov. 26, 2003 (5 pages).
United States Patent Office Action for U.S. Appl. No. 10/021,506 dated Sep. 7, 2004 (7 pages).
United States Patent Office Action for U.S. Appl. No. 10/021,506 dated Jun. 15, 2005 (5 pages).
United States Patent Office Action for U.S. Appl. No. 10/021,506 dated Nov. 21, 2005 (8 pages).

(Continued)

*Primary Examiner* — Paul V. Ward
(74) *Attorney, Agent, or Firm* — Michael Best & Friedrich LLP

(57) ABSTRACT

4-[3-(4-cyclopropanecarbonyl-piperazine-1-carbonyl)-4-fluoro-benzyl]-2H-phthalazin-1-one as crystalline Form A.

4 Claims, 3 Drawing Sheets

U.S. PATENT DOCUMENTS

| | | | |
|---|---|---|---|
| 2004/0044004 A1 | 3/2004 | Snutch et al. |
| 2004/0147529 A1 | 7/2004 | Snutch et al. |
| 2004/0192703 A1 | 9/2004 | Snutch et al. |
| 2004/0209872 A1 | 10/2004 | Snutch et al. |
| 2004/0242554 A1 | 12/2004 | Nilsson et al. |
| 2004/0259866 A1 | 12/2004 | Snutch et al. |
| 2004/0266784 A1 | 12/2004 | Snutch et al. |
| 2005/0020583 A1 | 1/2005 | Pulici |
| 2005/0054568 A1 | 3/2005 | Ling et al. |
| 2005/0059663 A1 | 3/2005 | Martin et al. |
| 2005/0227999 A1 | 10/2005 | Pajouhesh et al. |
| 2005/0277629 A1 | 12/2005 | Lansbury et al. |
| 2006/0030557 A1 | 2/2006 | Haviv et al. |
| 2006/0084660 A1 | 4/2006 | Snutch et al. |
| 2006/0142293 A1 | 6/2006 | Martin et al. |
| 2006/0276391 A1 | 12/2006 | Auricchio et al. |
| 2007/0093489 A1 | 4/2007 | Javaid et al. |
| 2007/0185105 A1 | 8/2007 | Snutch et al. |
| 2008/0146575 A1 | 6/2008 | Menear et al. |
| 2008/0255128 A1 | 10/2008 | Javaid et al. |
| 2010/0286157 A1 | 11/2010 | Quigley et al. |

FOREIGN PATENT DOCUMENTS

| | | |
|---|---|---|
| EP | 0389995 | 10/1990 |
| EP | 0502575 | 9/1992 |
| EP | 0590551 | 4/1994 |
| EP | 0634404 | 1/1995 |
| EP | 0699754 | 3/1996 |
| EP | 0705903 | 4/1996 |
| EP | 0792643 | 9/1997 |
| EP | 1477175 | 11/2004 |
| EP | 1760071 | 3/2007 |
| WO | WO 91/18591 | 12/1991 |
| WO | WO 94/10151 | 5/1994 |
| WO | WO 95/24379 | 9/1995 |
| WO | WO 96/19225 | 6/1996 |
| WO | WO 96/31501 | 10/1996 |
| WO | WO 97/36587 | 10/1997 |
| WO | WO 97/38664 | 10/1997 |
| WO | WO 97/45412 | 12/1997 |
| WO | WO 98/43477 | 10/1998 |
| WO | WO 99/08680 | 2/1999 |
| WO | WO 99/11624 | 3/1999 |
| WO | WO 99/11645 | 3/1999 |
| WO | WO 99/11649 | 3/1999 |
| WO | WO 99/44612 | 9/1999 |
| WO | WO 00/44726 | 8/2000 |
| WO | WO 00/67734 | 11/2000 |
| WO | WO 01/10856 | 2/2001 |
| WO | WO 01/12199 | 2/2001 |
| WO | WO 01/16136 | 3/2001 |
| WO | WO 01/16137 | 3/2001 |
| WO | WO 01/21615 | 3/2001 |
| WO | WO 01/23390 | 4/2001 |
| WO | WO 01/57038 | 8/2001 |
| WO | WO 01/79184 | 10/2001 |
| WO | WO 01/85686 | 11/2001 |
| WO | WO 01/85687 | 11/2001 |
| WO | WO 01/90077 | 11/2001 |
| WO | WO 02/36576 | 5/2002 |
| WO | WO 03/070726 | 5/2002 |
| WO | WO 02/44157 | 6/2002 |
| WO | WO 02/068407 | 9/2002 |
| WO | WO 02/090334 | 11/2002 |
| WO | WO 02/094790 | 11/2002 |
| WO | WO 03/007959 | 1/2003 |
| WO | WO 03/051879 | 6/2003 |
| WO | WO 03/055865 | 7/2003 |
| WO | WO 03/057145 | 7/2003 |
| WO | WO 03/070707 | 8/2003 |
| WO | WO 03/080581 | 10/2003 |
| WO | WO 03/093261 | 11/2003 |
| WO | WO 2004/080976 | * 4/2004 |
| WO | WO 2004/080976 | 9/2004 |
| WO | WO 2005/053662 | 6/2005 |
| WO | WO 2006/097176 | 9/2006 |
| WO | WO 2008/083027 | 7/2008 |

OTHER PUBLICATIONS

United States Patent Office Action for U.S. Appl. No. 11/352,178 dated Nov. 7, 2008 (11 pages).

United States Patent Office Action for U.S. Appl. No. 10/426,147 dated Oct. 28, 2004 (32 pages).

United States Patent Office Action for U.S. Appl. No. 10/426,147 dated Aug. 9, 2005 (16 pages).

United States Patent Office Action for U.S. Appl. No. 10/426,147 dated Apr. 25, 2006 (14 pages).

United States Patent Office Action for U.S. Appl. No. 11/873,671 dated Sep. 3, 2008 (35 pages).

United States Patent Office Action for U.S. Appl. No. 11/873,671 dated Mar. 6, 2009 (12 pages).

United States Patent Office Action for U.S. Appl. No. 12/143,208 dated May 8, 2009 (17 pages).

Affar, E. B. et al., "Immunodot blot method for the detection of poly(ADP-ribose) synthesized in vitro and in vivo," *Anal. Biochem* (1998) 259(2):280-283.

Ame, J-C. et al., "PARP-2, a novel mammalian DNA damage-dependent poly(ADP-ribose) polymerase," *J. Biol. Chem.* (1999) 274(25):17860-17868.

Angell, S.M. et al., "Consistent gene silencing in transgenic plants expressing a replicating potato virus X RNA," *EMBO J.* (1997) 16(12):3675-3684.

Arnaudeau, C. et al., "DNA double-strand breaks associated with replication forks are predominantly repaired by homologous recombination involving an exchange mechanism in mammalian cells," *J. Mol. Biol* (2001) 307:1235-1245.

Banasik, M. et al., "Specific Inhibitors of Poly (ADP-Ribose) Synthetase and Mono (ADP-Ribosyl) transferse", *J. Biol. Chem.*, 1992, vol. 267, 1569-1575.

Banasik, M. et al., "Inhibitors and activators of ADP-ribosylation reactions," *Mol. Cell Biochem.* (1994) 138:185-197.

Ben-Hur, E. et al., "Inhibitors of poly (ADP-ribose) synthesis enhance radiation response by differentially affecting repair of potentially lethal versus sublethal damage," *Br. J. Cancer* (1984) 49(VI):39-42.

Berge et al., 1977, "Pharmaceutically Acceptable Salts," *J. Pharm. Sci.*, vol. 66, 1-19. *Protective Groups in Organic Synthesis* (T. Green and P. Wuts, Wiley, 1991).

Berger, N. A. et al., "Poly (ADP-ribose) in cellular response to DNA damage", *Radiation Research*, 1985, vol. 101, 4-14.

Bhattacharyya, A. et al., "The breast cancer susceptibility gene BRCA1 is required for subnuclear assembly of Rad51 and survival following treatment with the DNA cross-linking agent cisplatin," *J. Biol. Chem.* (2000) 275(31: 23899-23903.

Bloch, W. et al., "Poly-adenosine diphosphate-ribose polymerase inhibition for myocardial protection: pathophysiologic and physiologic considerations," J. Thoracic Card. Surg. (2004) 128(2):323-324.

Bold, G. et al., "New anilinophthalazines as potent and orally well absorbed inhibitors of the FEBF receptor tyrosine kinases useful as antagonists of tumour-driven angiogenesis", *J. Med. Chem.*, 2000, vol. 43, No. 12, 2310-2323.

Braga, D. et al., "Making crystals from crystals: a green route to crystal engineering and polymorphism," Chem. Commun. (2005) 3635-3645.

Brummelkamp, T. R. et al., "A system for stable expression of short interfering RNAs in mammalian cells," *Science* (2002) 296:550-553.

Burzio, L. et al., "Poly (adenosine diphosphoribose) synthase activity of isolated nuclei of normal and leukemic leukocytes (38930)", *Proc. Soc. Exp. Bio. Med.*, 1975, vol. 149, 933-938.

Cantoni, O. et al., "Hydrogen peroxide insult in cultured mammalian cells: relationships between DNA single-strand breakage, poly (ADP-ribose) metabolism and cell killing", *Biochim. Biophys. Acta*, 1989, vol. 1014, 1-7.

Catteau, A. et al., "Methylation of the BRCA1 promoter region in sporadic breast and ovarian cancer: correlation with disease characteristics," *Oncogene* (1999) 18:1957-1965.

Chappuis, P. O. et al., "Risk Assessment and Genetic Testing," *Cancer Treat. Res.*, 2002, vol. 107, 29-59.

Cockcroft, X-L. et al., "Phthalazinones 2: optimisation and synthesis of novel potent inhibitors of poly(ADP-ribose)polymerase," Biorg. Med. Chem. Lett. (2006) 16:1040-1044.

Cosi, C. et al., "Poly (ADP-ribose) polymerase: early involvement in glutamate-induced neurotoxicity in cultured cerebellar granule cells", *J.Neurosci. Res.*, 1994, vol. 39, 38-46.

Cosi, C., "New inhibitors of poly(ADP-ribose) polymerase and their potential therapeutic targets," *Expert Opin. Ther. Patents* (2002) 12(7): 1047-1071.

Couzin, J., "The twists and turns in BRCA's path," *Science* (2003) 302:591-592.

Crooke, S.T., "Therapeutic applications of oligonucleotides," *Ann. Rev. Pharmacol. Toxicol.* (1992) 32:329-376.

Cuzzocrea, S., "Shock, inflammation and PARP," Pharmacological Res. (2005) 52:72-82.

D'Adda Di Fagagna, F. et al., "Functions of poly(ADP-ribose) polymerase in controlling telomere length and chromosomal stability", *Nature Gen.*, 1999, vol. 23, No. 1, 76-80.

D'Amours, D. et al., "Poly(ADP-ribosyl)ation reactions in the regulation of nuclear functions", *Biochem. J.*, 1999, vol. 342, 249-268.

D'Andrea, A. D. et al., "The fanconi anaemia/BRCA pathway," *Nat. Rev. Cancer* (2003) 3:23-34.

Dantzer, F. et al., "Base excision repair is imparied in mammalian cells lacking poly(ADP-ribose) polymerase-1," *Biochemistry* (2000) 39:7559-7569.

Davies, A. A. et al., "Role of BRCA2 in control of the RAD51 recombination and DNA repair protein," *Mol. Cell* (2001) 7:273-282.

Dillon, K. J. et al., "A flashplate assay for the identification of PARP-1 inhibitors," *J. Biomolecular Screening* (2003) 8(3):347-352.

Durkacz, B. W. et al., "(ADP-ribose)$_n$ participates in DNA excision repair", *Nature*, 1980, vol. 283, No. 7, 593-596.

Ehrlich, H.A. et al., "Recent advances in the polymerase chain reaction," *Science* (1991) 252:1643-1650.

Elbashir, S. M. et al., "Duplexes of 21-nucleotide RNAs mediate RNA interference in cultured mammalian cells," *Nature* (2001) 411:494-498.

El-Tamaty et al., Synthesis and biological activity of some 4-benzyl-1(2H)-phthalazinone derivatives, *Indian J. Chemistry*, v. 35B, 1067-1072 (1996).

Esteller, M. et al., "Promoter hypermethylation and BRCA1 inactivation in sporadic breast and ovarian tumors," *J. Natl. Cancer Inst.* (2000) 92(7):564-569.

Fire, A. et al., "Potent and specific genetic interference by double-stranded RNA in Caenorhabditis elegans," *Nature* (1998) 391:806-811.

Foray, N. et al., "A subset of ATM- and ATR-dependent phosphorylation events requires the BRCA1 protein," *Embo J.* (2003) 22(11):2860-2871.

Fuska, J. et al., "New Cytotoxic and antitumor agents," *Chemical Abstracts*, 104:102050 (1985).

Gaken, J. A. et al., "Efficient retroviral infection of mammalian cells is blocked by inhibition of poly(ADP-ribose) polymerase activity", *J. Virology*, 1996, vol. 70, No. 6, 3992-4000.

Gale, P.A. et al., "Calixpyrroles II," Coordination Chem. Rev. (2001) 222:57-102.

Gavezzotti, A., "Are crystal structures predictable?" Acc. Chem. Res. (1994) 27:309-314.

Greene, T.W. et al., Protective Groups in Organic Synthesis, Chapters 2 and 7, John Wiley & Sons Inc. (1999) p. 17-23 and 494-503.

Haber, J. E., "DNA recombination: the replication connection," *Trends Biochem. Sci.* (1999) 24:271-275.

Hall, I.H. et al., "Cytotoxicity of imides-N-alkyl semicarbazones, thiosemicarbazones, acetylhydrazones and related derivatives," *Anti-Cancer Drugs* (and abstract 122:204573), V.6, 147-153 (1995).

Hirai, K. et al., "Aberration of poly(adenosine diphosphate-ribose) metabolism in human colon adenomatous polyps and cancers", *Cancer Res.*, 1983, vol. 43, 3441-3446.

Hiramoto, T. et al., "Mutations of a novel human RAD54 homologue, RAD54B, in primary cancer," *Oncogene* (1999) 18:3422-3426.

Hoeijmakers, J. H.J., "Genome maintenance mechanisms for preventing cancer," *Nature* (2001) 411:366-374.

Hughes-Davies, L. et al., "EMSY links the BRCA2 pathway to sporadic breast and ovarian cancer," *Cell* (2003) 115:523-535.

Iino, M. et al., "Rational design and evaluation of new lead compound structures for selective .beta.ARK1 inhibitors," J. Med. Chem. (2002) 45(11):2150-2159.

Janatova, M. et al., "Detection of the most frequent mutations in BRCA1 gene on polyacrylamide gels containing spreadex polymer NAB," *Neoplasma* (2003) 50(4):246-250.

Jancarkova, N., "Detection and incidence of mutations of BRCA1 gene in patients with cancer of the breast and ovary," *Ceska Gynekol.* (2003) 68(1):11-16.

Jantzen and Robinson, "B. Prodrugs," taken from Modem Pharmaceutics, Third Edition, Banker and Rhodes, editors (1996) p. 596.

Jasin, M., "Homologous repair of DNA damage and tumorigenesis: the BRCA connection," *Oncogene* (2002) 21(58):8981-8993.

Kashani-Sabet, M. et al., "Application of ribozymes to cancer gene therapy," *Cancer Gene Therapy* (1995) 2(3):213-223.

Kawamura, I. et al., "Ponalrestat, an aldose reductase inhibitor," *Chemical Abstract* 132:273943.

Kerr, P. et al., "New complexities for BRCA1 and BRCA2," *Curr. Biol.* (2001) 11:R668-676.

Kerrigan, F. et al. "Imide-substituted 4-benzyl-2H-phthalazin-1-ones: potent inhibitors of poly(ADP-ribose) polymerase-1 (PARP-1)," Poster at 12th Sci-RSC Medicinal Chemistry Symposium, Cambridge, 7-10 (2003).

Khanna, K. K. et al., "DNA double-strand breaks: signaling, repair and the cancer connection," *Nat. Genet.* (2001) 27(3):247-254.

Kraakman-Van Der Zwet, M. et al., "Brca2 (XRCC11) deficiency results in radioresistant DNA synthesis and a higher frequency of spontaneous deletions," *Mol. Cell Biol.* (2002) 22(2):669-679.

Lakhani, S. R. et al., "The pathology of familial breast cancer: predictive value of immunohistochemical markers estrogen receptor, progesterone receptor, HER-2, and p53 in patients with mutations in BRCA1 and BRCA2," *J. Clin. Oncol.* (2002) 20(9):2310-2318.

Le Rhun, Y. et al., "Cellular responses to DNA damage in the absence of poly(ADP-ribose)polymerase", *Biochem. Biophys. Res. Commun.*, 1998, vol. 245, 1-10.

Lemay, M. et al., "Detection of DNA damage and identification of UV-induced photoproducts using the cometassay kit," *Biotechniques* (1999) 27:846-851.

Liaudet, L. et al., "Protection against hemorrhagic shock in mice genetically deficient in poly(ADP-ribose)polymerase", *Proc. Natl. Acad. Sci. U.S.A.*, 2000, vol. 97, No. 3, 10203-10208.

Loh, V.M. et al., "Phthalazinones. Part 1: The design and synthesis of a novel series of potent inhibitors of poly(ADP-ribose)polymerase," Bioorg. Med. Chem. Lett. (2005) 15:2235-2238.

Martin, N. et al., "Phthalazinone derivatives as potent PARP-1 inhibitors", 13th *Intl. Symposium on ADP-ribosylation*, 2001, Abstract 107.

Martin, N. et al., "DNA repair inhibition and cancer therapy," *J. Photochem. and PhotoBiol. B: Biology* (2001) 63:162-170.

Matsuda, M. et al., "Mutations in the RAD54 recombination gene in primary cancers," *Oncogene*(1999) 18:3427-3430.

Menear, K.A. et al., "4-[3-(4-cyclopropanecarbonylpiperazine-1-carbonyl)-4-fluorobenzyl]-2H-phthalazin-1-one: a novel bioavailable inhibitor of poly(ADP-ribose) polymerase-1," J. Med. Chem. (Published on Web (Sep. 19, 2008) A-K.

Menissier De Murcia, J. et al., "Requirement of poly(ADP-ribose)polymerase in recovery from DNA damage in mice and cells", *Proc. Natl. Acad. Sci. U.S.A.*, 1997, vol. 94, 7303-7307.

Mercola, D. et al., "Antisense approaches to cancer gene therapy," *Cancer Gene Therapy* (1995) 2(1):47-59.

Miller, B.A., "Inhibition of TRPM2 function by PARP inhibitors protects cells from oxidative stress-induced death," Br. J. Pharmacology (2004) 143:515-516.

Miwa, M. et al., "Cell density-dependent increase in chromatin-associated ADP-ribosyltransferase activity in simian virus 40-transformed cells", *Arch. Biochem. Biophys.*, 1977, vol. 181, 313-321.

Moynahan, M. E. et al., "Brca1 controls homology-directed DNA repair," *Mol. Cell* (1999) 4:511-518.

Moynahan, M. E. et al., "BRCA2 is required for homology-directed repair or chromosomal breaks," *Mol. Cell* (2001) 7:263-272.

Mullis, K. et al., "Specific enzymatic amplification of DNA in vitro: the polymerase chain reaction," *Cold Spring Harbor Symp. Quant. Biol.* (1987) 51:263-273.

Nathanson, K. L. et al., "Breast cancer genetics: what we know and what we need," *Nat. Med.* (2001) 7(5):552-556.

Neuhausen, S. L. et al., "Mutation testing of early-onset breast cancer genes BRCA1 and BRCA2," *Genet. Test* (1997) 1(2):75-83.

Noel, G. et al., "Poly(ADP-ribse) polymerase (PARP-1) is not involved in DNA double-strand break recovery," *BMC Cell Biol.* (2003) 4:7-17.

Perkins, E. et al., "Novel inhibitors of poly(ADP-ribose)polymerase/ PARP1 and PARP2 identified using a cell-based screen in yeast", *Cancer Res.*, vol. 61, 4175-4183 (2001).

Radice, P. J., "Mutations of BRCA genes in hereditary breast and ovarian cancer," *Exp. Clin. Cancer Res.* (2002) 21(3 Suppl.):9-12.

Rattan, S. I. et al., "Kinetin delays the onset of ageing characteristics in human fibroblasts", *Biochem. Biophys. Res. Commun.*, 1994, vol. 201, No. 2, 665-672.

Said, S. I. et al., "Excitotoxicity in the lung: N-methy-D-aspartate-induced, nitric oxide-dependent, pulmonary edema is attenuated by vasoactive intestinal peptide and by inhibitors of poly(ADP-ribose)polymerase", *Proc. Natl. Acad. Sci. U.S.A.*, 1996, vol. 93, 4688-4692.

Schlicker, A. et al., "4-Amino-1,8-napthalimide: a novel inhibitor of poly(ADP-ribose)polymerase and radiation sensitizer", *Int. J. Radiat. Bio.*, 1999, vol. 75, No. 1, 91-100.

Schultz, N. et al., "Poly(ADP-ribose) polymerase (PARP-1) has a controlling role in homologous recombination," *Nucleic Acids Res.* (2003) 31:4959-4964.

Shall, S. et al., "Poly(ADP-ribose) polymerase-1: what have we learned from the deficient mouse model?" *Mutat. Res.* (2000) 460:1-15.

Shimizu, T. et al., "Inhibitory effects of azelastine and tranilast on leukotriene $B_4$ and leukotriene $C_4$ generation by rat colonic mucosa", *Prostaglandins Leukotrienes and Essential Fatty Acids*, 1995, vol. 53, 355-358.

Skehan, P. et al., "New colorimetric cytotoxicity assay for anticancer-drug screening", *J. Natl. Cancer Inst.*, 1990, vol. 82, No. 13, 1107-1112.

Southan, G.J. and Szabo, C., "Poly (ADP-ribose) polymerase inhibitors," *Current Medicinal Chemistry*, 10:4, 321-340 (2003).

Spears, L.G. Jr. et al., "Anionic phosphorous as a nucleophile. An anion chain arbuzov mechanism," *J. Org. Chem.* (1987) 52:61-64.

Suto, M.J. et al., "Dihydroisoquinolinones: the design and synthesis of a new series of potent inhibitors of poly(ADP-ribose) polymerase," *Anticancer Drug Des.* (1991) 7:107-117.

Szabo, C. et al., "Endothelial dysfunction in a rat model of endotoxic shock", *J. Clin. Invest.*, 1997, vol. 100, 723-25.

Szabo, G. et al., "Poly-ADP-ribose polymerase inhibition protects against myocardial and endothelial reperfusion injury after hypothermic cardiac arrest," *J. Thoracic Cardiovas. Surg.* (2003) 126(3):651-658.

Taniguchi, T. et al., "Disruption of the Fanconi anemia-BRCA pathway in cisplatin-sensitive ovarian tumors," *Nat. Med.* (2003) 9(5):568-574.

Tarsounas, M. et al., "BRCA2-dependent and independent formation of RAD51 nuclear foci," *Oncogene* (2003) 22:1115-1123.

Tasatargil, A. et al., "Poly(ADP-ribose) polymerase inhibition prevents homocysteine-induced endothelial dysfunction in the isolated rat aorta," *Pharmacology* (2004) 72:99-105.

Thompson, L. H. et al., "Recombinational DNA repair and human disease," *Mutat. Res.* (2002) 509:49-78.

Tracey, W. et al., "Aldose reductase inhibition alone or combined with an adenosine A3 agonist reduces ischemic myocardial injury," *Chemical Abstract* (2000) 134:65983.

Tutt, A. et al., "The relationship between the roles of BRCA genes in DNA repair and cancer predisposition," *Trends Mol. Med.* (2002) 8(12):571-576.

Tutt, A. et al., "Mutation in Brca2 stimulates error-prone homology-directed repair of DNA double-strand breaks occurring between repeated sequences," EMBO J. (2001) 20(17):4704-4716.

Tutt, A N.J. et al., "Disruption of Brca2 increases the spontaneous mutation rate in vivo: synergism with ionizing radiation," *Embo Reports* (2002) 3(3):255-260.

Uhlmann, E. et al., Antisense oligonucleotides: a new therapeutic principle, *Chem. Rev.* (1990) 90(4):543-584.

Venkitaraman, A. R., "Cancer susceptibility and the functions of BRCA1 and BRCA2," *Cell* (2002) 108:171-182.

Vippagunta, S.R. et al., "Crystalline solids," Adv. Drug Delivery Reviews (2001) 48:3-26.

Voinnet, O. et al. "Systemic signalling in gene silencing," *Nature* (1997) 389:553.

Wang, Z.-Q. et al., "Mice lacking ADPRT and poly(ADP-ribosyl)ation develop normally but are susceptible to skin disease", *Genes Dev.*, 1995, vol. 9, 509-520.

Wang, Z.-Q. et al., "PARP is important for genomic stability but dispensable in apoptosis," *Genes Dev.* (1997) 11:2347-2358.

Wood, R.D. et al., "Human DNA repair genes," *Science* (2001) 291:1284-1289.

Yamaguchi, M. et al., "Novel antiasthmatic agents with dual activities of thromboxane $A_2$ synthetase inhibition and bronchodilation. 1. 2-[2-(1-Imidazolyl)alkyl]-1(2H)-phthalazinones", *J. Med. Chem.*, 1993, vol. 36, No. 25, 4052-4060.

Yamaguchi, M. et al., "Novel antiasthmatic agents with dual activities of thromboxane $A_2$ synthetase inhibition and bronchodilation. 2. 4-(3-Pyridyl)-1(2H)-phthalazinones", *J. Med. Chem.*, 1993, vol. 36, No. 25, 4061-4068.

Zamore, P. D., "RNAi: double-stranded RNA directs the ATP-dependent cleavage of mRNA at 21 to 23 nucleotide intervals," *Cell* (2000) 101:25-33.

Zamore, P. D., "RNA interference: listening to the sound of silence," *Nature Structural Biology* (2001) 8(9):746-750.

Zhang, W. et al., "Fluorous 2,4-dichloro-1,3,5-triazine (F-DCT) as amide coupling agent," QSAR Comb Sci. (2006) 25(8-9):724-727.

Zhong, Q. et al., "Association of BRCA1 with the hRad50-hMrel1-p95 complex and the DNA damage response," *Science* (1999) 285:747-750.

McMahon, G., "VEGF receptor signaling in tumor angiogenesis," *The Oncologist* (2000) 5(suppl 1):3-10.

Pinedo et al., "Translation research . . . " *The Oncologist* (2000) 5(suppl 1):1-2.

United States Office Action for U.S. Appl. No. 11/352,178 dated Jun. 17, 2009 (9 pages).

United States Office Action for U.S. Appl. No. 10/876,080 dated Jun. 23, 2005 (4 pages).

United States Office Action for U.S. Appl. No. 10/876,080 dated Jul. 12, 2006 (5 pages).

United States Office Action for U.S. Appl. No. 10/876,080 dated Jan. 5, 2007 (5 pages).

United States Office Action for U.S. Appl. No. 10/876,080 dated Oct. 4, 2007 (6 pages).

United States Office Action for U.S. Appl. No. 11/318,155 dated Jul. 11, 2008 (10 pages).

United States Office Action for U.S. Appl. No. 11/318,155 dated Jan. 26, 2009 (9 pages).

United States Patent Office Notice of Allowance for U.S. Appl. No. 12/738,181 dated Dec. 29, 2011 (10 pages).

US 6,759,401, 07/2004, Nilsson et al. (withdrawn)

* cited by examiner

Chemical shift (ppm)

PHTHALAZINONE DERIVATIVE

CROSS-REFERENCE TO RELATED APPLICATIONS

This application is a Continuation of U.S. application Ser. No. 11/873,671, filed Oct. 17, 2007, which claims priority to U.S. Provisional Application No. 60/829,694, filed Oct. 17, 2006, which are incorporated herein by reference in their entireties.

The present invention relates to a crystalline form and improved methods of synthesis of a particular phthalazinone derivative, intermediates in the synthesis and pharmaceutical compositions and uses of the crystalline form.

The mammalian enzyme PARP (a 113-kDa multidomain protein) has been implicated in the signalling of DNA damage through its ability to recognize and rapidly bind to DNA single or double strand breaks (D'Amours, et al., Biochem. J., 342, 249-268 (1999)).

Several observations have led to the conclusion that PARP participates in a variety of DNA-related functions including gene amplification, cell division, differentiation, apoptosis, DNA base excision repair and also effects on telomere length and chromosome stability (d'Adda di Fagagna, et al., Nature Gen., 23(1), 76-80 (1999)).

Studies on the mechanism by which PARP modulates DNA repair and other processes has identified its importance in the formation of poly (ADP-ribose) chains within the cellular nucleus (Althaus, F. R. and Richter, C., ADP-Ribosylation of Proteins: Enzymology and Biological Significance, Springer-Verlag, Berlin (1987)). The DNA-bound, activated PARP utilizes NAD to synthesize poly (ADP-ribose) on a variety of nuclear target proteins, including topoisomerase, histones and PARP itself (Rhun, et al., Biochem. Biophys. Res. Commun., 245, 1-10 (1998))

Poly (ADP-ribosyl)ation has also been associated with malignant transformation. For example, PARP activity is higher in the isolated nuclei of SV40-transformed fibroblasts, while both leukemic cells and colon cancer cells show higher enzyme activity than the equivalent normal leukocytes and colon mucosa (Miwa, et al., Arch. Biochem. Biophys., 181, 313-321 (1977); Burzio, et al., Proc. Soc. Exp. Biol. Med., 149, 933-938 (1975); and Hirai, et al., Cancer Res., 43, 3441-3446 (1983)).

A number of low-molecular-weight inhibitors of PARP have been used to elucidate the functional role of poly (ADP-ribosyl)ation in DNA repair. In cells treated with alkylating agents, the inhibition of PARP leads to a marked increase in DNA-strand breakage and cell killing (Durkacz, et al., Nature, 283, 593-596 (1980); Berger, N. A., Radiation Research, 101, 4-14 (1985)).

Subsequently, such inhibitors have been shown to enhance the effects of radiation response by suppressing the repair of potentially lethal damage (Ben-Hur, et al., British Journal of Cancer, 49 (Suppl. VI), 34-42 (1984); Schlicker, et al., Int. J. Radiat. Bioi., 75, 91-100 (1999)). PARP inhibitors have been reported to be effective in radio sensitising hypoxic tumour cells (U.S. Pat. No. 5,032,617; U.S. Pat. No. 5,215,738 and U.S. Pat. No. 5,041,653).

Furthermore, PARP knockout (PARP-/-) animals exhibit genomic instability in response to alkylating agents and γ-irradiation (Wang, et al., Genes Dev., 9, 509-520 (1995); Menissier de Murcia, et al., Proc. Natl. Acad. Sci. USA, 94, 7303-7307 (1997)).

A role for PARP has also been demonstrated in certain vascular diseases, septic shock, ischaemic injury and neurotoxicity (Cantoni, et al., Biochim. Biophys. Acta, 1014, 1-7 (1989); Szabo, et al., J. Clin. Invest., 100, 723-735 (1997)). Oxygen radical DNA damage that leads to strand breaks in DNA, which are subsequently recognised by PARP, is a major contributing factor to such disease states as shown by PARP inhibitor studies (Cosi, et al., J. Neurosci. Res., 39, 38-46 (1994); Said, et al., Proc. Natl. Acad. Sci. U.S.A., 93, 4688-4692 (1996)). More recently, PARP has been demonstrated to play a role in the pathogenesis of haemorrhagic shock (Liaudet, et al., Proc. Natl. Acad. Sci. U.S.A., 97(3), 10203-10208 (2000)).

It has also been demonstrated that efficient retroviral infection of mammalian cells is blocked by the inhibition of PARP activity. Such inhibition of recombinant retroviral vector infections was shown to occur in various different cell types (Gaken, et al., J. Virology, 70(6), 3992-4000 (1996)). Inhibitors of PARP have thus been developed for the use in anti-viral therapies and in cancer treatment (WO 91/18591).

Moreover, PARP inhibition has been speculated to delay the onset of aging characteristics in human fibroblasts (Rattan and Clark, Biochem. Biophys. Res. Comm., 201(2), 665-672 (1994)). This may be related to the role that PARP plays in controlling telomere function (d'Adda di Fagagna, et al., Nature Gen., 23(1), 76-80 (1999)).

WO 2004/080976 discloses a number of phthalazinone derivatives, their activity in inhibiting PARP, and their consequential use in treating cancer, whether as an adjunct to radiotherapy or chemotherapy, or as a stand alone agent.

WO 2005/053662 describes the use of PARP inhibitors, in particular phthalazinone derivatives, as base excision repair (BER) inhibitors. The use of these inhibitors in the manufacture of medicaments for the treatment of cancers which are deficient in Homologous Recombination (HR) dependent DNA DSB repair activity, in particular for cancers which have a BRCA1 and/or a BRCA2 deficient phenotype, is described.

4-[3-(4-Cyclopropanecarbonyl-piperazine-1-carbonyl)-4-fluoro-benzyl]-2H-phthalazin-1-one (compound A) disclosed in WO 2004/080976:

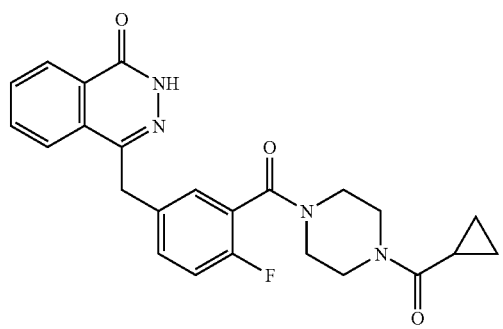

A is of particular interest.

In WO 2004/080976, compound A was synthesised as one of a number of library compounds from 4-[4-fluoro-3-(piperazine-1-carbonyl)-benzyl]-2H-phthalazin-1-one (compound B):

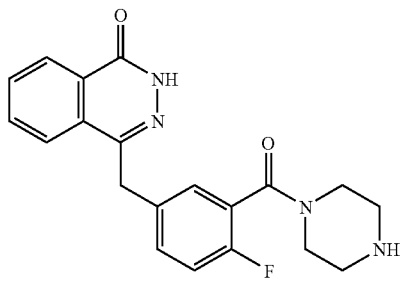

B by the addition of cyclopropanecarbonyl chloride:

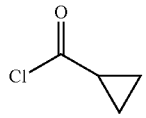

to a solution of (B) in dichloromethane, followed by Hünig's base (N,N-diisopropylethyl amine). This reaction is carried out with stirring at room temperature for 16 hours, and the resulting compound being purified by preparative HPLC.

The piperazine derivative (B) was prepared by deprotecting 4-[2-fluoro-5-(4-oxo-3,4-dihydro-phthalazin-1-ylmethyl)-benzoyl]-piperazine-1-carboxylic acid tert-butyl ester (compound C):

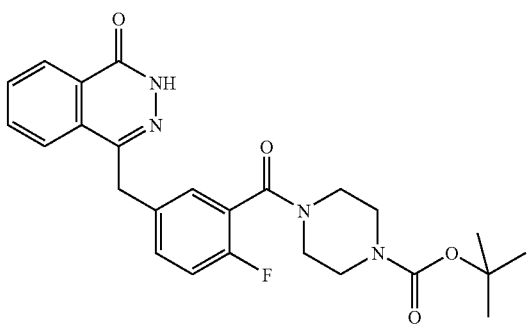

C by the use of 6M HCl and ethanol for 1 hour, followed by basification with ammonia to pH 9, and extraction into dichloromethane.

The Boc-protected piperazine derivative (C) was prepared from 2-fluoro-5-(4-oxo-3,4-dihydro-phthalazin-1-ylmethyl)-benzoic acid (compound D):

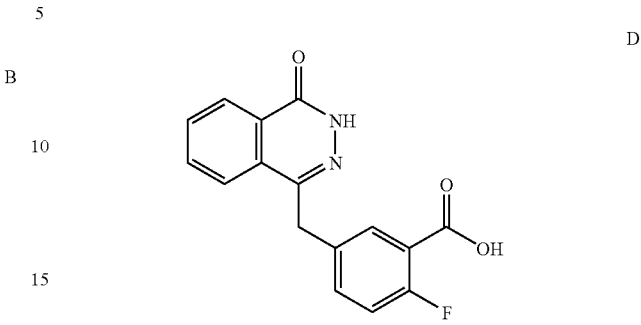

D by the addition of piperazine-1-carboxylic acid tert-butyl ester:

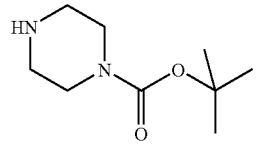

2-(1H-benzotriazol-1-yl)-1,1,3,3-tetramethyluronium hexafluorophosphate (HBTU) and N,N,-diisopropylethylamine in dimethylacetamide, followed by stirring for 18 hours.

Particular forms of compound A may have advantageous properties, for example with regard to their solubility and/or their stability and/or their bioavailability and/or their impurity profile and/or their filtration characteristics and/or their drying characteristics and/or their lack of hygroscopicity, and/or they may be easier to handle and/or micronise and/or form into tablets. It is also desired to have an improved method of synthesis that is suitable for synthesis of compound A on a multi-gram scale.

Accordingly, a first aspect of the present invention provides 4-[3-(4-cyclopropanecarbonyl-piperazine-1-carbonyl)-4-fluoro-benzyl]-2H-phthalazin-1-one (compound A) substantially in crystalline form, and in particular in Form A.

"Substantially in crystalline form" as used above, means that at least 50% by weight of compound A is in crystalline form, preferably at least 70% by weight, 80% or 90% by weight. In some embodiments, at least 95% by weight, 99% by weight or even 99.5% or more by weight may be in crystalline form.

Compound A as crystalline Form A has an X-ray diffraction pattern ($\lambda=1.5418$ Å) containing specific peaks at:

| Peak | 2θ° (±0.1°) |
| --- | --- |
| 1 | 12.0 |
| 2 | 17.8 |
| 3 | 21.1 |
| 4 | 22.3 |
| 5 | 29.2 |

Compound A as crystalline form A may also have the following additional peaks an X-ray diffraction pattern (λ=1.5418 Å):

| Peak | 2θ° (±0.1°) |
| --- | --- |
| 6 | 10.5 |
| 7 | 14.0 |
| 8 | 21.7 |
| 9 | 24.3 |
| 10 | 26.1 |

Compound A as crystalline Form A may also be characterised by any combination of three or more peaks selected from the list of 10 peaks above.

A representative powder XRD pattern of compound A as Form A is shown in FIG. 3.

Without wishing to be bound by theory, compound A is able to readily form a structure in which solvent molecules can occupy positions within the crystal lattice. Such solvates, not necessarily stoichiometric in nature, can consist of one pure solvate (e.g. Compound A methanolate, and Compound A Tetrahydrofuranate) or potentially can consist of more than one solvent component (e.g. methanol and di-ethyl ether). The solvent molecules typically lie within pockets created by the Compound A molecules. In certain circumstances, the volume of these pockets are sufficiently flexible to incorporate a range of solvents, resulting in little change in the overall structure of the material, and hence only small shifts in the XRPD reflections.

Solvates, including those which share the same overall structure, arise from solution maturation and crystallisation experiments from dichloromethane, ethyl acetate, methanol, ethanol, isopropanol, 2-butanone, t-butyl methyl ether, toluene, tetrahydrofuran, water, cyclohexane, cyclopropyl methyl ketone, 1,2 dichloroethane, ethyl trifluoroacetate, fluorobenzenehexafluoro-iso-propanol, methyl nonafluorobutyl ether, 2-methyl-1-propanol, nitromethane, propionitrile, trichloroethylene, ααα-trifluorotoluene, heptane, dioxane, acetonitrile, either as pure solvents or when combined with another solvent. The X-ray diffraction pattern of the most common solvate structure is shown in FIG. 4, and typically contains most intense peaks at positions listed below:

| Peak | 2θ° (±0.1°) (λ = 1.5418 Å) |
| --- | --- |
| 1 | 7.0-7.5 |
| 2 | 10.1-10.6 |
| 3 | 15.1-15.6 |
| 4 | 18.5-19.0 |
| 5 | 21.0-21.5 |
| 6 | 24.8-25.3 |
| 7 | 27.0-27.5 |

It will be understood that the relative intensities of peaks shown in the figures may vary according to the orientation of the sample under test and on the type and setting of the instrument used so that the intensities in the XRD traces included herein are illustrative and not intended to be used for absolute comparison.

Form A of compound A is substantially free from solvent. The term "substantially free from solvent" as used herein refers to the form having only insignificant amounts of any solvent, e.g. a form with a total of 0.5% by weight or less of any solvent. The total amount of any solvent, including water, may be 0.25%, 0.1%, 0.05% or 0.025% by weight or less.

Form A of compound A may also be characterised using DSC. Form A of compound A when heated from 25° C. to 325° C. at 10° C. per minute will begin melting at 210.1° C.±1° C. A representative DSC trace for compound A as Form A is shown in FIG. 5.

The second aspect of the present invention provides a method of obtaining 4-[3-(4-cyclopropanecarbonyl-piperazine-1-carbonyl)-4-fluoro-benzyl]-2H-phthalazin-1-one (compound A) as crystalline Form A which comprises crystallising compound A in a solvent and then displacing the solvent from the crystalline form with a displacing agent. The displacing agent may be water or a mixture of a $C_{1-2}$ alcohol and water.

In a first embodiment, this method comprises the steps of:
(i) crystallising 4-[3-(4-cyclopropanecarbonyl-piperazine-1-carbonyl)-4-fluoro-benzyl]-2H-phthalazin-1-one (compound A) from a solvent;
(ii) if the original solvent is not ethanol, treating the crystalline compound A with ethanol;
(iii) treating the crystalline compound A with water to remove trapped ethanol;
(iv) drying the resulting product.

The solvent used in the original crystallisation may be, for example, dichloromethane or acetonitrile.

The methods for obtaining Form A may generally involve solvent replacement. It has been found that compound A crystallises in such a way that channels in the crystal lattice are formed which can trap solvents, thus making them difficult to remove.

The method of the first embodiment can be used in particular if the solvent used in the crystallisation of compound A is dichloromethane. The step of exchanging the dichloromethane as a solvent with ethanol as a solvent can be carried out by distilling the solution of compound A at atmospheric pressure in the presence of ethanol. The exchange is complete when the head temperature approaches the boiling point of ethanol, e.g. at least 73° C. In particular, the exchange may be carried out by distilling out the majority of the DCM, then adding a volume of ethanol. The distillation is then continued, with replacing batches of distillate with equal volumes of ethanol.

Crystallising compound A from the ethanol solvent may be carried out by cooling the solution to below 15° C., preferably less than 10° C., and more preferably to about 8° C. The crystals of compound A may then be removed from solution by filtration.

The crystalline compound A may be treated with water to remove trapped ethanol by suspended the crystalline material in water and heating at reflux for a sufficient time, for example at least three hours, and preferably for about four hours. The crystalline compound A may be removed from suspension in water by filtration.

Drying the resulting product of the above step is readily achieved. For example, by heating the product in an oven at a temperature of at least 60° C., preferably at about 70° C.

In another such embodiment, the method comprises the steps of:
(i) obtaining compound A as crystalline form containing solvent;
(ii) if the original solvent used in the synthesis of compound A in the crystalline form is not a mixture of water and a $C_{1-2}$ alcohol (i.e. methanol, ethanol), treating compound A in the crystalline form with a mixture of water and a $C_{1-2}$ alcohol;
(ii) drying the resulting product.

The resulting product can be further treated with a mixture of water and a $C_{1-2}$ alcohol, and dried in order to further isolate compound A in a crystalline Form A.

The mixture of water and $C_{1-2}$ alcohol is preferably in the range of 2:1 to 1:2 by volume, and more preferably 1.5:1 to 1:1.5 by volume. A particularly preferred mixture is 1 part water to 1.2 parts $C_{1-2}$ alcohol. Another particularly preferred mixture is 2 parts water to 1 part $C_{1-2}$ alcohol. The $C_{1-2}$ alcohol is preferably ethanol.

Compound A as crystalline Form may be obtained by crystallisation of the compound A from a solvent, as described above.

The solvent treatment in step (ii) may be carried out by suspending compound A in the mixture of water and $C_{1-2}$ alcohol and heating to reflux with stirring. This may be followed by cooling to between 55 and 65° C. and filtering, e.g. through a celite pad. The filter pad may be washed with a mixture of water and $C_{1-2}$ alcohol before being distilled at ambient pressure (usually 1 atm), or above. The distillation may be stopped to yield a suspension that is left at room temperature before subsequent filtration. The resulting filter cake may be washed with water.

Drying the resulting product of the above step is readily achieved. For example, by heating the product in an oven at a temperature of at least 50° C., preferably at about 60° C.

The further treatment may proceed in a similar manner to that described above.

In a third embodiment, the method comprises:

(i) suspending compound A in a mixture of water and a $C_{1-2}$ alcohol as the solvent;

(ii) heating the suspension to reflux;

(iii) cooling the solution and seeding with compound A as Form A;

(iv) drying the resulting product.

The resulting product can be further treated with a mixture of water and a $C_{1-2}$ alcohol, and dried in order to further isolate compound A in a crystalline Form A.

The mixture of water and $C_{1-2}$ alcohol is preferably in the range of 2:1 to 1:5 by volume, and more preferably 1:2 to 1:4 by volume. A particularly preferred mixture is 1 part water to 3 parts $C_{1-2}$ alcohol. The $C_{1-2}$ alcohol is preferably ethanol.

Step (iii) may comprise cooling the solution to between 65 and 75° C. (e.g. 70° C.) and filtering, e.g. through a celite pad. The filter pad may be washed with a mixture of water and $C_{1-2}$ alcohol before being distilled (e.g. at ambient pressure, or above). The seeding may occur after the resulting filtrate has been cooled to between 40 and 50° C. (e.g. 45° C.). The resulting suspension may be cooled to ambient temperature (e.g. 20° C.) in between 2 and 3 hours (e.g. 2.5 hours) and maintained at said temperature for long enough to establish crystallisation. This may be between 12 and 24 hours, and may be for about 16 hours. At the end of this period, further water may be added. The amount may be about equal to the volume of total solvent (water and $C_{1-2}$ alcohol) present and may be added slowly, for example over a period of 4 to 6 (e.g. 5) hours. The suspension may be held at ambient temperature after the water addition, for example for 2 hours.

The suspension may then be filtered, and the resulting filter cake may be washed with a mixture of $C_{1-2}$ alcohol and water (in a ratio of between 1:3 and 1:2, e.g. 1:2.3).

Drying the resulting product of the above step is readily achieved. For example, by heating the product in an oven under vacuum at a temperature of between 40 and 60° C.

A third aspect of the present invention provides a method of synthesising compound A from compound B comprising the step of:

(i) adding a pre-mixed solution of triethylamine and cyclopropane carbonyl chloride, in an appropriate organic solvent (for example, DCM (dichloromethane)) in a controlled manner, to compound B in the same organic solvent with the temperature of the solution being controlled to be below 20° C.

In some embodiments, the method further comprises the step of:

(ii) agitating (e.g. stirring) the resulting solution from (i) until the reaction is complete, whilst maintaining the temperature of the solution below 20° C.

The addition in step (i) may take place in a dropwise manner

This method is more controlled than that described in WO 2004/080976, resulting in a more regioselective addition of the acid chloride. The less controlled method of the prior art can lead to addition of the acid chloride at the phthalazinone nitrogen and or oxygen, as well as at the desired piperidine nitrogen.

It is preferred that the above method is carried out under a nitrogen atmosphere.

It is further preferred that the temperature of the solution in stage (ii) is maintained between 10 and 15° C.

The product of the above reaction is preferably worked up by at least one water washing step. More preferably the work up contains an initial and final water washing steps, and intermediate washing steps using a dilute acid, e.g. 5% citric acid solution, followed by a dilute base, e.g. 5% sodium carbonate solution.

A fourth aspect of the present invention provides a method of synthesising compound A from compound D comprising reacting compound D with 1-(cyclopropylcarbonyl)piperazine, or a mineral acid salt thereof, in the presence of an amide coupling agent and a base, for example, an amine (e.g. a tertiary amine, such as diisopropylethylamine).

The mineral acid salt may be, for example, the hydrochloride salt.

The addition of 1-(cyclopropylcarbonyl)piperazine, or a mineral acid salt thereof, to compound D may be carried out in any suitable solvent, for example, acetonitrile. The amide coupling agent is preferably 2-(1H-benzotriazol-1-yl)-1,1,3,3-tetramethyluronium hexafluorophosphate (HBTU). It is preferably added to the solution of 1-(cyclopropylcarbonyl) piperazine, or its mineral acid salt, diisopropylethylamine and compound D over a period of time, for example 30 minutes. The temperature of the resulting solution may be maintained at 25° C. or below (or 20° C. or below, e.g. at 18° C.). After its addition, the resulting solution may be left to stand for a period of time. A preferred temperature regime is holding the solution at room temperature for 2 hours.

The resulting compound A may be removed from the solution by cooling to below 10° C. (or below 5° C., for example, 3° C.) for a period of time (e.g. 1 hour), followed by filtration. The resulting compound A may be washed, for example, with cold acetonitrile.

In WO 2004/080976, the following route to compound D is disclosed:

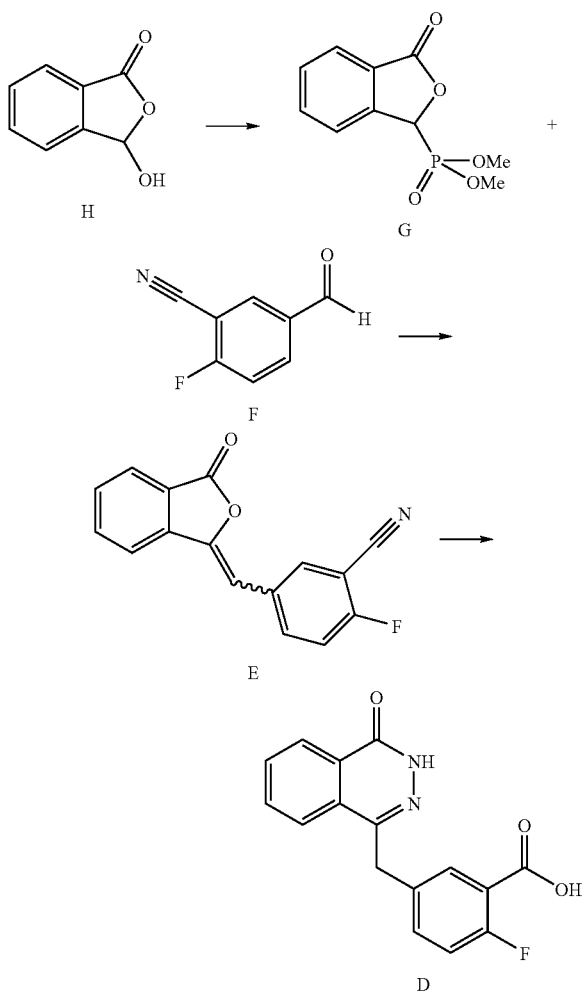

Dimethyl phosphite was added drop-wise to a solution of sodium methoxide in methanol at 0° C. 2-Carboxybenzaldehyde (H) was then added portion-wise to the reaction mixture as a slurry in methanol, with the temperature kept below 5° C. The resulting pale yellow solution was warmed to 20° C. over 1 hour. Methanesulphonic acid was added to the reaction drop-wise and the resulting white suspension was evaporated in vacuo. The white residue was quenched with water and extracted into chloroform. The combined organic extracts were washed with water, dried over $MgSO_4$, and evaporated in vacuo to yield (3-oxo-1,3-dihydro-isobenzofuran-1-yl) phosphonic acid dimethyl ester (G) as a white solid (yield: 95%). This was then used without further purification in the next stage.

To a mixture of (3-oxo-1,3-dihydro-isobenzofuran-1-yl) phosphonic acid dimethyl ester (G) in tetrahydrofuran and 2-fluoro-5-formylbenzonitrile (F) in tetrahydrofuran was added triethylamine drop-wise over 25 min, with the temperature kept below 15° C. The reaction mixture was warmed slowly to 20° C. over 1 hour and concentrated in vacuo. The white residue was slurried in water or 30 minutes, filtered, washed with water, hexane and ether, and dried to yield 2-fluoro-5-(3-oxo-3H-isobenzofuran-1-ylidenemethyl)benzonitrile (E) as a 50:50 mixture of E and Z isomers (yield: 96%).

To a suspension of 2-fluoro-5-(3-oxo-3H-isobenzofuran-1-ylidenemethyl)benzonitrile (E) in water was added aqueous sodium hydroxide solution and the reaction mixture was heated under nitrogen to 90° C. for 30 minutes. The reaction mixture was partially cooled to 70° C., and hydrazine hydrate was added and stirred for 18 hours at 70° C. The reaction was cooled to room temperature and acidified with 2M HCl to pH 4. The mixture was stirred for 10 minutes and filtered. The resulting solid was washed with water, hexane, ether, ethyl acetate and dried to yield compound D as a pale pink powder (yield: 77%).

It is also desired to have an improved method of synthesis of compound D.

Accordingly a fifth aspect of the present invention provides a method synthesising compound D, comprising the step of:

(a) synthesising diethyl (3-oxo-1,3-dihydro-2-benzofuran-1-yl)phosphonate (G') from 2-carboxybenzaldehyde (H);

(b) synthesising 2-fluoro-5-[(E/Z)-(3-oxo-2-benzofuran-1(3H)-ylidene)methyl]benzonitrile (E) from diethyl (3-oxo-1,3-dihydro-2-benzofuran-1-yl)phosphonate.

It is preferred that compound G' is not isolated in the synthesis. This method avoids the use of the sodium salt of dimethylphosphite which is unstable (Pelchowicz, et al., *J. Chem. Soc*, 4348-4350 (1961)) in alcoholic solution. It is preferred that the step (a) occurs in 2-methyltetrahydrofuran in which the sodium salt of diethyl phosphite is stable. This salt may be formed in situ by adding diethyl phosphite to a cooled solution of sodium t-amylate in 2-methyltetrahydrofuran. The reaction with the sodium salt of diethyl phosphite may be followed by reaction with methanesulphonic acid.

Step (b) may be carried out in 2-methyltetrahydrofuran, with the addition of triethylamine.

The method of synthesising compound D may further comprise the step of:

(c) synthesising 2-fluoro-5-[(4-oxo-3,4-dihydrophthalazin-1-yl)methyl]benzonitrile (ED):

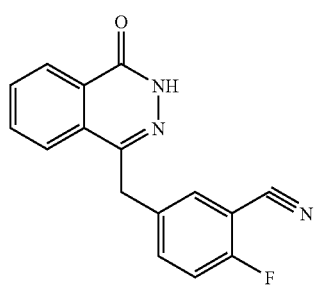

from compound E by reaction with hydrazine hydrate; and (d) synthesising compound D from compound ED by reaction with sodium hydroxide.

Step (c) may be achieved by using between 1.1 and 1.3 equivalents of hydrazine hydrate in tetrahydrofuran followed by neutralisation of the excess hydrazine hydrate using acetic acid.

A sixth aspect of the present invention provides the compound ED:

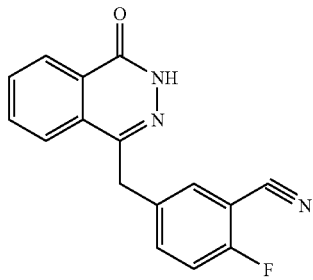

and its use in the synthesis of compound D.

A further aspect of the invention provides a mineral acid salt of 1-(cyclopropylcarbonyl) piperazine, and a method of synthesis thereof by reacting piperazine with acetic acid, followed by addition of cyclopropanecarbonyl chloride.

A seventh aspect of the present invention provides a pharmaceutical composition comprising a compound of the first aspect and a pharmaceutically acceptable carrier or diluent.

An eighth aspect of the present invention provides a compound of the first aspect for use in a method of treatment of the human or animal body.

A ninth aspect of the present invention provides the use of a compound as defined in the first aspect of the invention in the preparation of a medicament for inhibiting the activity of PARP.

Further aspects of the invention provide the use of a compound as defined in the first aspect of the invention in the preparation of a medicament for the treatment of: vascular disease; septic shock; ischaemic injury; neurotoxicity; haemorraghic shock; viral infection; or diseases ameliorated by the inhibition of the activity of PARP.

Another further aspect of the invention provides for the use of a compound as defined in the first aspect of the invention in the preparation of a medicament for use as an adjunct in cancer therapy or for potentiating tumour cells for treatment with ionizing radiation or chemotherapeutic agents.

Other further aspects of the invention provide for the treatment of disease ameliorated by the inhibition of PARP, comprising administering to a subject in need of treatment a therapeutically-effective amount of a compound as defined in the first aspect, preferably in the form of a pharmaceutical composition and the treatment of cancer, comprising administering to a subject in need of treatment a therapeutically-effective amount of a compound as defined in the first aspect in combination, preferably in the form of a pharmaceutical composition, simultaneously or sequentially with ionizing radiation or chemotherapeutic agents.

In further aspects of the present invention, the compounds may be used in the preparation of a medicament for the treatment of cancer which is deficient in Homologous Recombination (HR) dependent DNA DSB repair activity, or in the treatment of a patient of a cancer which is deficient in HR dependent DNA DSB repair activity, comprising administering to said patient a therapeutically-effective amount of the compound.

The HR dependent DNA DSB repair pathway repairs double-strand breaks (DSBs) in DNA via homologous mechanisms to reform a continuous DNA helix (K. K. Khanna and S. P. Jackson, Nat. Genet. 27(3): 247-254 (2001)). The components of the HR dependent DNA DSB repair pathway include, but are not limited to, ATM (NM_000051), RAD51 (NM_002875), RAD51L1 (NM_002877), RAD51C (NM_002876), RAD51L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS1 (NM_002485). Other proteins involved in the HR dependent DNA DSB repair pathway include regulatory factors such as EMSY (Hughes-Davies, et al., Cell, 115, pp 523-535). HR components are also described in Wood, et al., Science, 291, 1284-1289 (2001).

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterised in the art (see for example, Wood, et al., Science, 291, 1284-1289 (2001)) and include the components listed above.

In some preferred embodiments, the cancer cells may have a BRCA1 and/or a BRCA2 deficient phenotype i.e. BRCA1 and/or BRCA2 activity is reduced or abolished in the cancer cells. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (Hughes-Davies, et al., Cell, 115, 523-535).

BRCA1 and BRCA2 are known tumour suppressors whose wild-type alleles are frequently lost in tumours of heterozygous carriers (Jasin M., Oncogene, 21(58), 8981-93 (2002); Tutt, et al., Trends Mol Med., 8(12), 571-6, (2002)). The association of BRCA1 and/or BRCA2 mutations with breast cancer is well-characterised in the art (Radice, P. J., Exp Clin Cancer Res., 21(3 Suppl), 9-12 (2002)). Amplification of the EMSY gene, which encodes a BRCA2 binding factor, is also known to be associated with breast and ovarian cancer.

Carriers of mutations in BRCA1 and/or BRCA2 are also at elevated risk of cancer of the ovary, prostate and pancreas.

In some preferred embodiments, the individual is heterozygous for one or more variations, such as mutations and polymorphisms, in BRCA1 and/or BRCA2 or a regulator thereof. The detection of variation in BRCA1 and BRCA2 is well-known in the art and is described, for example in EP 699 754, EP 705 903, Neuhausen, S. L. and Ostrander, E. A., Genet. Test, 1, 75-83 (1992); Chappnis, P. O. and Foulkes, W. D., Cancer Treat Res, 107, 29-59 (2002); Janatova M., et al., Neoplasma, 50(4), 246-50 (2003); Jancarkova, N., Ceska Gynekol., 68(1), 11-6 (2003)). Determination of amplification of the BRCA2 binding factor EMSY is described in Hughes-Davies, et al., Cell, 115, 523-535).

Mutations and polymorphisms associated with cancer may be detected at the nucleic acid level by detecting the presence of a variant nucleic acid sequenc or at the protein level by detecting the presence of a variant (i.e. a mutant or allelic variant) polypeptide.

USE

Figure 1:
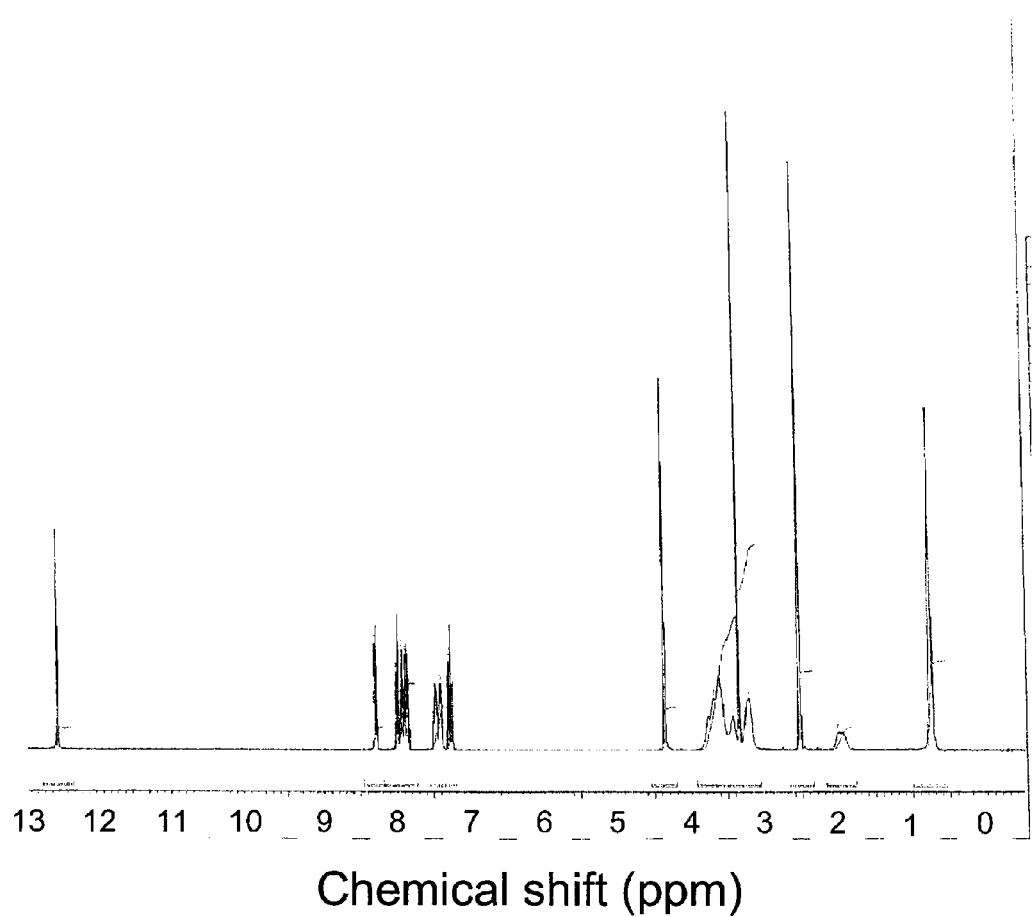
FIG. 1 shows the NMR of compound A after water treatment (example 1)

The present invention provides compound A as Form A as an active compound, specifically, active in inhibiting the activity of PARP.

The term "active" as used herein, pertains to the compound which is capable of inhibiting PARP activity. One assay which may conveniently be used in order to assess the PARP inhibition offered by the compound is described in the examples below.

The present invention further provides a method of inhibiting the activity of PARP in a cell, comprising contacting said cell with an effective amount of the active compound, preferably in the form of a pharmaceutically acceptable composition. Such a method may be practised in vitro or in vivo.

For example, a sample of cells may be grown in vitro and the active compound brought into contact with said cells, and the effect of the compound on those cells observed. As examples of "effect", the amount of DNA repair effected in a certain time may be determined. Where the active compound is found to exert an influence on the cells, this may be used as a prognostic or diagnostic marker of the efficacy of the compound in methods of treating a patient carrying cells of the same cellular type.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "adjunct" as used herein relates to the use of the active compound in conjunction with known therapeutic means. Such means include cytotoxic regimes of drugs and/or ionising radiation as used in the treatment of different cancer types. In particular, the active compounds are known to potentiate the actions of a number of cancer chemotherapy treatments, which include the topoisomerase class of poisons (e.g. topotecan, irinotecan, rubitecan), most of the known alkylating agents (e.g. DTIC, temozolamide) and platinum based drugs (e.g. carboplatin, cisplatin) used in treating cancer.

The active compound may also be used as cell culture additives to inhibit PARP, for example, in order to sensitize cells to known chemotherapeutic agents or ionising radiation treatments in vitro.

The active compound may also be used as part of an in vitro assay, for example, in order to determine whether a candidate host is likely to benefit from treatment with the compound in question.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

Formulations

While it is possible for the active compound to be administered alone, it is preferable to present it as a pharmaceutical composition (e.g., formulation) comprising the active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing the active compound, as defined above, together with one or more pharmaceutically acceptable carriers, excipients, buffers, adjuvants, stabilisers, or other materials, as described herein, such that active compound remains as crystalline Form A.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, diluents, excipients, etc. can be found in standard pharmaceutical texts. See, for example, "Handbook of Pharmaceutical Additives", 2nd Edition (eds. M. Ash and I. Ash), 2001 (Synapse Information Resources, Inc., Endicott, N.Y., USA), "Remington's Pharmaceutical Sciences", 20th edition, pub. Lippincott, Williams & Wilkins, 2000; and "Handbook of Pharmaceutical Excipients", 2nd edition, 1994.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of suspensions, tablets, granules, powders, capsules, cachets, pills or pastes.

Formulations suitable for oral administration (e.g., by ingestion) may be presented as discrete units such as capsules, cachets or tablets, each containing a predetermined amount of the active compound; as a powder or granules; as a suspension in an aqueous or non-aqueous liquid; or as a paste.

A tablet may be made by conventional means, e.g. compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

A capsule may include the active compound in suspension.

Formulations suitable for topical administration (e.g. transdermal, intranasal, ocular, buccal, and sublingual) may be formulated as a paste.

Formulations suitable for topical administration to the eye also include eye drops wherein the active compound is suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose.

Formulations suitable for administration by inhalation include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Dosage

It will be appreciated that appropriate dosages of the active compound, and compositions comprising the active compound, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 10 mg to about 600 mg per $m^2$ body area weight of the subject per day.

EXAMPLES

Example 1

Synthesis of Compound A

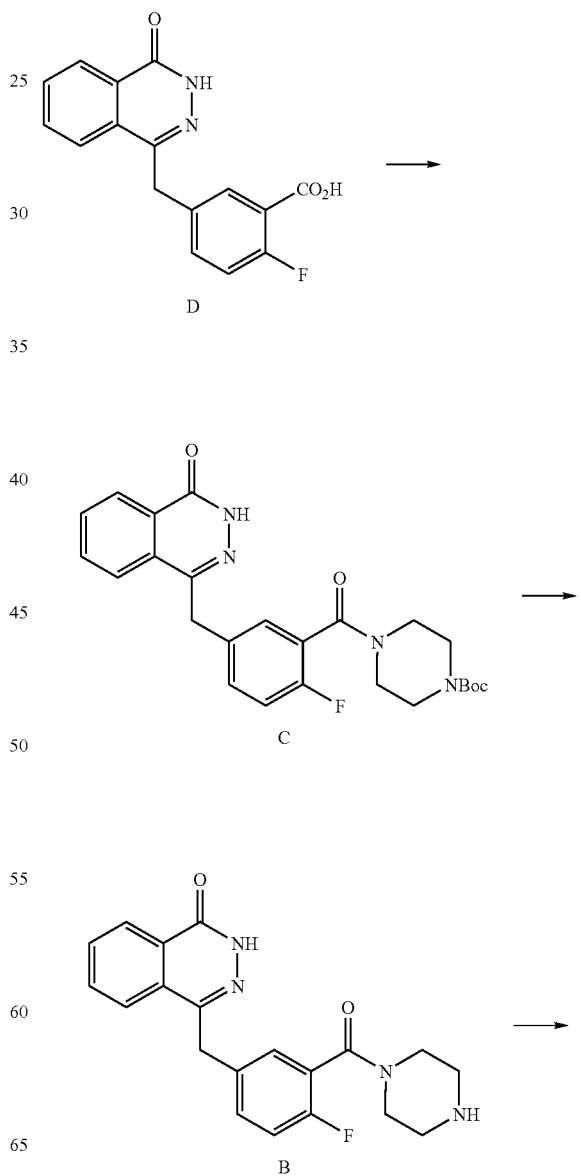

-continued

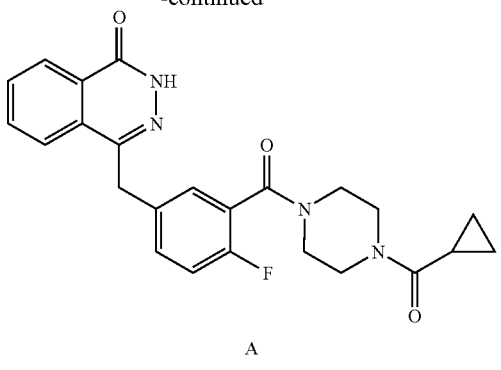

A

Starting material (D) was synthesised by the method disclosed in WO 2004/080976

Methods

Preparative HPLC

Samples were purified with a Waters mass-directed purification system utilising a Waters 600 LC pump, Waters Xterra C18 column (5 μm 19 mm×50 mm) and Micromass ZQ mass spectrometer, operating in positive ion electrospray ionisation mode. Mobile phases A (0.1% formic acid in water) and B (0.1% formic acid in acetonitrile) were used in a gradient; 5% B to 100% over 7 min, held for 3 min, at a flow rate of 20 ml/min.

Analytical HPLC-MS

Analytical HPLC was carried out with a Spectra System P4000 pump and Jones Genesis C18 column (4 μm, 50 mm×4.6 mm). Mobile phases A (0.1% formic acid in water) and B (acetonitrile) were used in a gradient of 5% B for 1 min rising to 98% B after 5 min, held for 3 min at a flow rate of 2 ml/min. Detection was by a TSP UV 6000LP detector at 254 nm UV and range 210-600 nm PDA. The Mass spectrometer was a Finnigan LCQ operating in positive ion electrospray mode.

NMR $^1$H NMR spectra were recorded using Bruker DPX 300 spectrometer at 300 MHz. Chemical shifts were reported in parts per million (ppm) on the δ scale relative to tetramethylsilane internal standard. Unless stated otherwise all samples were dissolved in DMSO-$d_6$.

(a) 4-[2-Fluoro-5-(4-oxo-3,4-dihydro-phthalazin-1-ylmethyl)-benzoyl]-piperazine-1-carboxylic acid tert-butyl ester (C)

To a stirred solution of the starting material D (850 g) in dimethylacetamide (DMA) (3561 ml) at room temperature under nitrogen was added HBTU (2-(1H-benzotriazol-1-yl)-1,1,3,3-tetramethyluronium hexafluorophosphate) (1402 g) in one portion. Hünig's base (iPr$_2$NEt, 1096 ml) was then added with the temperature kept between 15 to 25° C. followed by a solution of 1-Boc-piperazine (637 g) in DMA (1428 ml) with the temperature kept between 15 to 25° C.

The solution was stirred at room temperature for 2 hours and sampled for completion (HPLC). Upon completion the solution was added to vigorously stirred water (17085 ml) with the temperature kept between 15 to 25° C. and the solid filtered off, washing with water (2×7131 ml), hexane (2×7131 ml) and methyl tert-butyl ether (MTBE) (2×3561 ml). The solid was then dried overnight and then sampled for water content and chemical purity.

This reaction was then repeated, see table:

| Batch | Yield (g) | Purity (HPLC Area %) | Water Content (K.F.) | Corrected yield |
|---|---|---|---|---|
| 1 | 1571.3 | 86.80 | 24.3 | 1032.5 g (78%) |
| 2 | 2781.6 | 85.00 | 40.3 | 1411.5 g (106%) | a. Greater than 100% yield attributed to non-representative sampling (b) 4-[4-Fluoro-3-(piperazine-1-carbonyl)-benzyl]-2H-phthalazin-1-one (B)

To a stirred solution of industrial methylated spirits (IMS) (2200 ml) and concentrated HCl (4400 ml) was added compound C (2780.2 g) in portions at room temperature under nitrogen, the foaming was controlled by the addition rate. The solution was then stirred at 15 to 25° C. for 30 minutes and sampled for completion (HPLC).

Upon completion the solution was evaporated to remove any IMS and the aqueous extracted with CH$_2$Cl$_2$ (2×3500 ml) before the pH was adjusted to >8 using concentrated ammonia. The resultant slurry was then diluted with water (10000 ml) and extracted with CH$_2$Cl$_2$ (4×3500 ml), washed with water (2×2000 ml), dried over MgSO$_4$ (250 g) and evaporated. The crude product was then slurried in CH$_2$Cl$_2$ (3500 ml) and added to MTBE (5000 ml). The resultant suspension was filtered and dried at 50° C. overnight yielding 611.0 g (58.5% yield) of material with a purity of 94.12%

(c) 4-[3-(4-Cyclopropanecarbonyl-piperazine-1-carbonyl)-4-fluoro-benzyl]-2H-phthalazin-1-one (A)

To a stirred suspension of compound B (1290 g) in CH$_2$Cl$_2$ (15480 ml) under nitrogen was added a pre-mixed solution of triethylamine (470 ml) and cyclopropane carbonyl chloride (306 ml) in CH$_2$Cl$_2$ (1290 ml) dropwise with the temperature kept below 20° C. The solution was then stirred at 10-15° C. for 15 minutes and sampled for completion. The reaction mixture was found to contain only 1.18% of starting material B and so the reaction was deemed complete and the batch was then worked-up.

The reaction mixture was washed with water (7595 ml), 5% citric acid solution (7595 ml), 5% sodium carbonate solution (7595 ml) and water (7595 ml). The organic layer was then dried over magnesium sulfate (500 g).

The CH$_2$Cl$_2$ containing product layer was then isolated, filtered through Celite and charged to a 25l vessel. CH$_2$Cl$_2$ (8445 ml) was then distilled out at atmospheric pressure and ethanol (10000 ml) added. Distillation was then continued with every 4000 ml of distillate that was removed being replaced with ethanol (4000 ml) until the head temperature reached 73.7° C. The reaction volume was then reduced (to 7730 ml) by which time the head temperature had reached 78.9° C. and the solution was allowed to cool to 8° C. overnight. The solid was then filtered off, washed with ethanol (1290 ml) and dried at 70° C. overnight. Yield=1377.3 g (90%). HPLC purity (99.34% [area %]). Contained 4.93% ethanol and 0.45% CH$_2$Cl$_2$ by GC.

(d) Water Treatment of Compound A

A suspension of compound A (1377.0 g), as produced by the method of Example 1, in water (13770 ml) was heated to reflux for 4 hours, cooled to room temperature and filtered. The solid was washed with water (2754 ml) and dried at 70°

C. overnight. Yield=1274.8 g (92.6%). HPLC purity (99.49% [area %]). Contained 0.01% ethanol and 0.01% $CH_2Cl_2$ by GC.

$^1$H NMR spectrum of compound A (DMSO-d6) following the water treatment is shown in FIG. 1.

Figure 2:
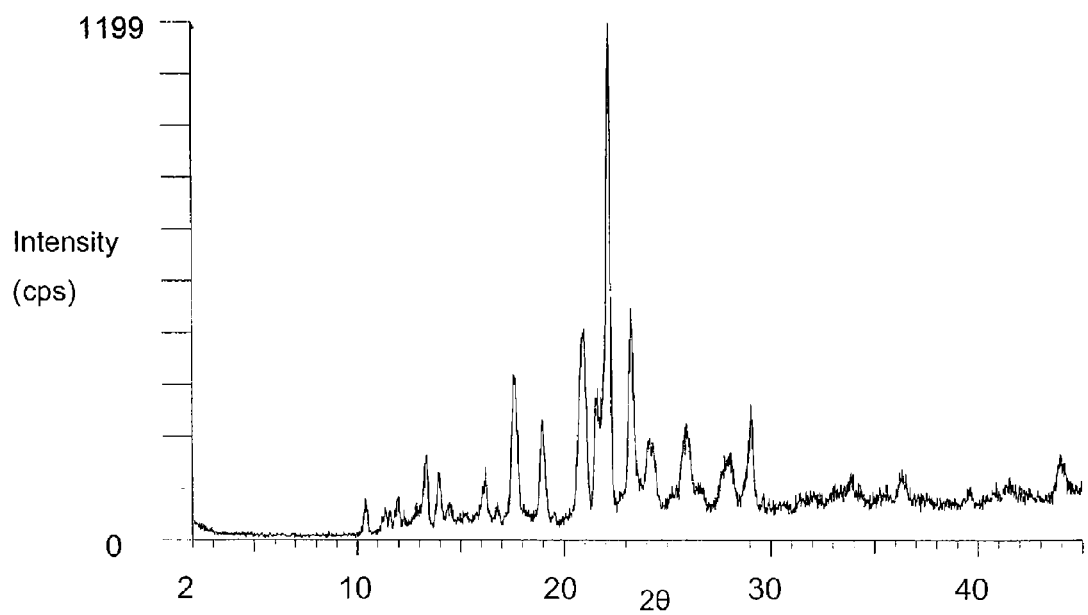
FIG. 2 shows the powder XRD pattern of compound A as Form A after water treatment (example 1)

The powder XRD pattern of Compound A following the water treatment is shown in FIG. 2, which shows the compound is as Form A.

Example 2

Alternative Synthesis of Compound A Using 1-(cyclopropylcarbonyl) piperazine

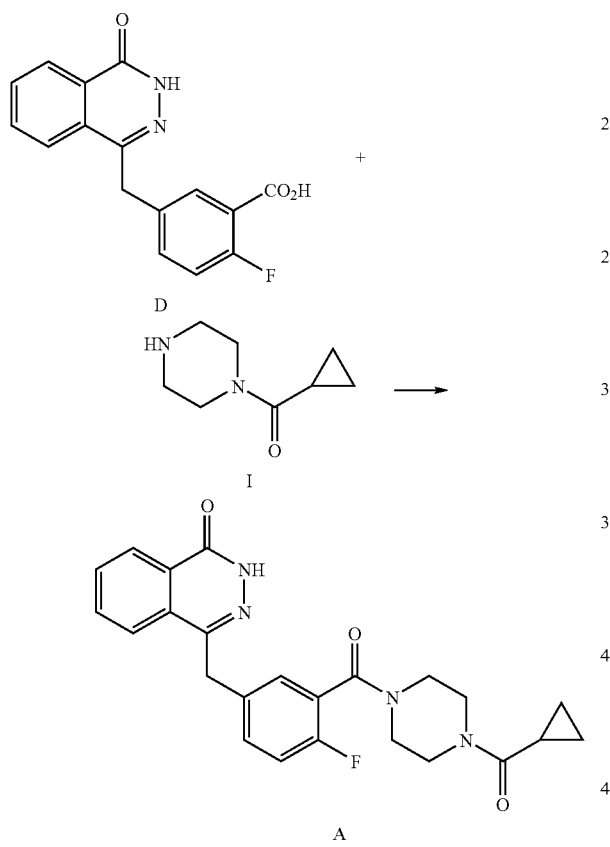

Methods (also for Examples 3 & 4)

NMR $^1$H NMR spectra were recorded using Bruker DPX 400 spectrometer at 400 MHz. Chemical shifts were reported in parts per million (ppm) on the δ scale relative to tetramethylsilane internal standard. Unless stated otherwise all samples were dissolved in DMSO-$d_6$.

Mass Spectra

Mass spectra were recorded on an Agilent XCT ion trap mass spectrometer using tandem mass spectrometry (MS/MS) for structural confirmation. The instrument was operated in a positive ion elctrospray mode.

(a) 4-[3-(4-Cyclopropanecarbonyl-piperazine-1-carbonyl)-4-fluoro-benzyl]-2H-phthalazin-1-one (Compound A)

2-Fluoro-5-[(4-oxo-3,4-dihydrophthalazin-1-yl)methyl] benzoic acid (D)(15.23 g, 51.07 mmol) was suspended with stirring under nitrogen in acetonitrile (96 ml). Diisopropylethylamine (19.6 ml, 112.3 mmol) was added followed by 1-cyclopropylcarbonylpiperazine (1)(9.45 g, 61.28 mmol) and acetonitrile (1 ml). The reaction mixture was cooled to 18° C. O-Benzotriazol-1-yl-tetramethyluronium hexafluorophosphate (25.18 g, 66.39 mmol) was added over 30 minutes and the reaction mixture was stirred for 2 hours at room temperature. The reaction mixture was cooled to 3° C. and maintained at this temperature for 1 hour, before being filtered. The filter cake was washed with cold (3° C.) acetonitrile (20 ml) before being dried in vacuo at up to 40° C. to give the title compound as a pale yellow solid (20.21 g).

Mass Spectrum: MH+435

1H NMR (400 MHz. DMSO-d6) δ: 0.70 (m, 4H), 1.88 (br s, 1H), 3.20 (br s, 2H), 3.56 (m, 6H), 4.31 (s, 2H), 7.17 (t, 1H), 7.34 (dd, 1H), 7.41 (m, 1H), 7.77 (dt, 1H), 7.83 (dt, 1H), 7.92 (d, 1H), 8.25 (dd, 1H), 12.53 (s, 1H).

Example 3

Alternative Synthesis of Compound A Using 1-(cyclopropylcarbonyl) piperazine HCl salt

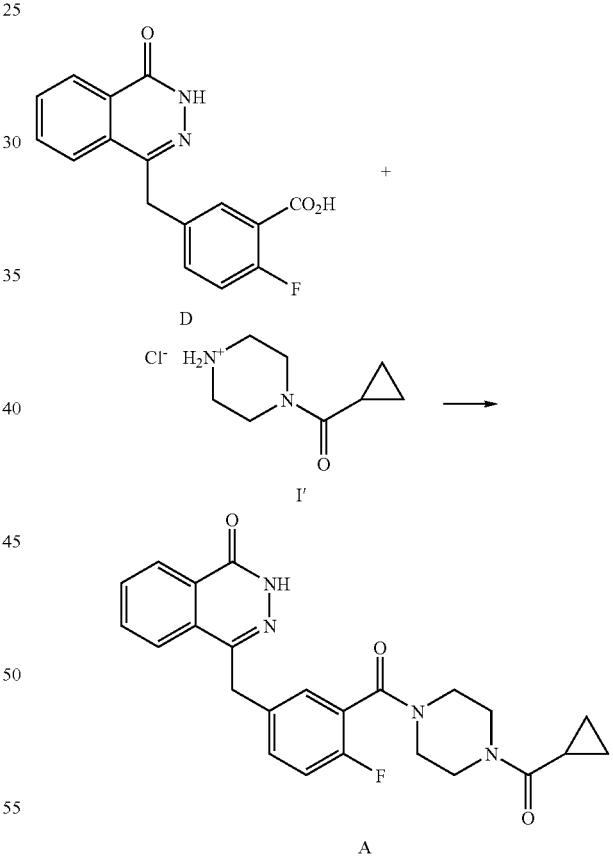

(a) 1-(Cyclopropylcarbonyl)piperazine HCl salt (I')

Acetic acid (700 ml) was treated with piperazine (50.00 g, 0.581 mol) portionwise over 15 minutes with stirring under nitrogen The reaction mixture was warmed to 40° C. and maintained at this temperature until a complete solution was obtained. Cyclopropanecarbonyl chloride 59.2 ml, 0.638 mol) was added over 15 minutes. The reaction mixture was stirred at room temperature overnight. The reaction mixture was filtered and the filtrate distilled under reduced pressure until ~430 ml of distillates had been collected. Toluene (550 ml) was charged to the reaction mixture and reduced pressure distillation continued until a further 400 ml of distillates were collected. A further charge of toluene (550 ml) was added and reduced pressure distillation continued until 350 ml of distillates were collected. The resulting slurry was diluted with toluene (200 ml) and stirred overnight. Further toluene (500 ml) was added in order to mobilise the slurry. The slurry was filtered, washed with toluene (100 ml) and dried in vacuo at 40° C. to give the title compound as an off white solid (86.78 g).

Mass Spectrum: MH+155

$^1$H NMR (400 MHz. D$_2$O) δ: 0.92 (m, 4H), 1.98 (m, 1H), 3.29 (m, 2H), 3.38 (m, 2H), 3.84 (m, 2H), 4.08 (m, 2H).

(b) Compound A

2-Fluoro-5-[(4-oxo-3,4-dihydrophthalazin-1-yl)methyl] benzoic acid (D)(0.95 g, 3.19 mmol) was suspended with stirring under nitrogen in acetonitrile (4 ml). 2-(1H-benzotriazol-1-yl)-1,1,3,3-tetramethyluronium hexafluorophosphate (HBTU) (1.45 g, 3.83 mmol) was added followed by 1-cyclopropylcarbonylpiperazine HCl salt (I')(0.73 g, 3.83 mmol). Diisopropylethylamine (1.39 ml, 7.98 mmol) was added over 3 minutes and the reaction mixture was stirred for overnight at room temperature. The reaction mixture was cooled to 5° C. and maintained at this temperature for 1 hour, before being filtered. The filter cake was washed with cold (3° C.) acetonitrile (2 ml) before being dried in vacuo at up to 40° C. to give the title compound as a pale yellow solid (0.93 g).

(c) Recrystallisation of Compound A from Aqueous Methanol

Compound A (9.40 g, 21.64 mmol) from step (b) was suspended in a mixture of water (100 ml) and methanol (120 ml). The suspension was heated to reflux with stirring. The hazy solution produced was then cooled to 60° C. and filtered through a pad of harborlite. The filter pad was washed with a mixture of water (5 ml) and methanol (5 ml). The filtrate was distilled at atmospheric pressure until 115 ml of distillate had been collected. Distillation was then stopped and the suspension produced allowed to cool to room temperature. The resultant suspension was stirred for ~18 hours before being filtered. The filter cake was washed with water (20 ml), before being dried in vacuo at up to 60° C. to give the title compound in Form A as a white solid (8.67 g).

Mass Spectrum: MH+435

1H NMR (400 MHz, DMSO-d6) δ: 0.70 (m, 4H), 1.88 (br s, 1H), 3.20 (br s, 2H), 3.56 (m, 6H), 4.31 (s, 2H), 7.17 (t, 1H), 7.34 (dd, 1H), 7.41 (m, 1H), 7.77 (dt, 1H), 7.83 (dt, 1H), 7.92 (d, 1H), 8.25 (dd, 1H), 12.53 (s, 1H).

(d) Recrystallisation of Compound A from Aqueous Ethanol

Compound A (9.40 g, 21.64 mmol) from step (b) was suspended in a mixture of water (100 ml) and ethanol (50 ml). The suspension was heated to reflux with stirring. The hazy solution produced was then cooled to 60° C. and filtered through a pad of harborlite. The filter pad was washed with a mixture of water (5 ml) and ethanol (5 ml). The filtrate was distilled at atmospheric pressure until 53 ml of distillate had been collected. Distillation was then stopped and the suspension produced allowed to cool to room temperature. The resultant suspension was stirred for ~18 hours before being filtered. The filter cake was washed with water (20 ml), before being dried in vacuo at 60° C. to give the title compound in Form A as a white solid (8.74 g).

Mass Spectrum: MH+435

$^1$H NMR (400 MHz, DMSO-d6) δ: 0.70 (m, 4H), 1.88 (br s, 1H), 3.20 (br s, 2H), 3.56 (m, 6H), 4.31 (s, 2H), 7.17 (t, 1H), 7.34 (dd, 1H), 7.41 (m, 1H), 7.77 (dt, 1H), 7.83 (dt, 1H), 7.92 (d, 1H), 8.25 (dd, 1H), 12.53 (s, 1H).

Example 4

Alternative Synthesis of Compound D

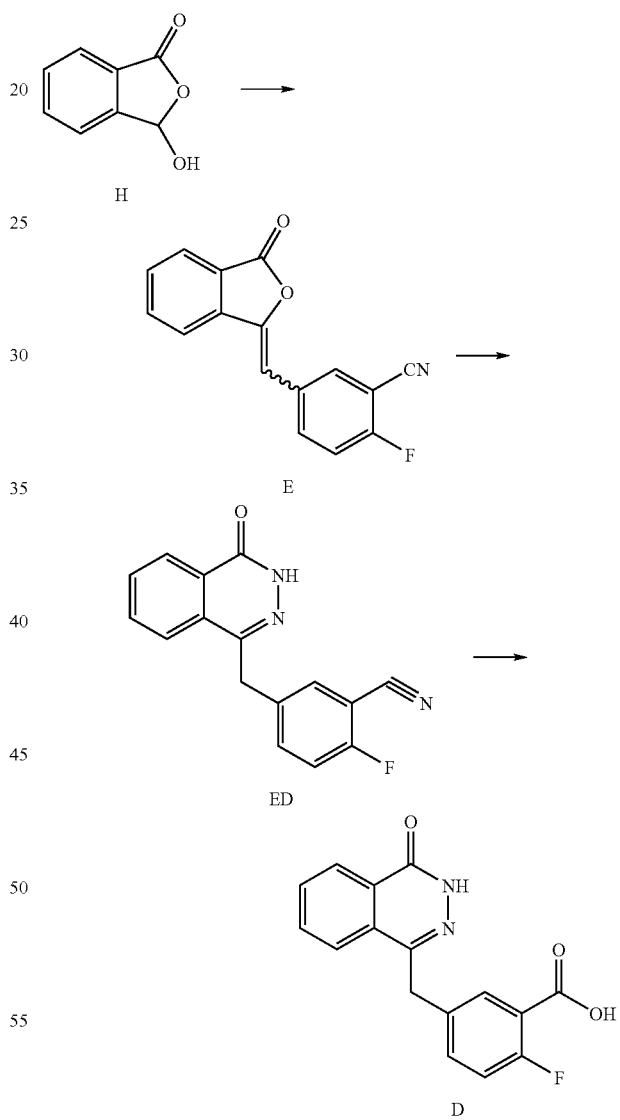

(a) 2-Fluoro-5-[(E/Z)-(3-oxo-2-benzofuran-1(3H)-ylidene)methyl]benzonitrile (E)

Sodium t-amylate (99.00 g, 0.854 mol) and 2-methyltetrahydrofuran (960 ml) were cooled to 2° C. under a nitrogen atmosphere. Diethyl phosphite (110 ml, 0.855 mol) was added dropwise maintaining the temperature at <5° C. 2-Methyltetrahydrofuran (40 ml) was added as line wash. The reaction was stirred at 2° C. for 1 hour 40 minutes. A solution of 2-carboxybenzaldehyde (H)(80 g, 0.533 mol) in 2-methyltetrahydrofuran (200 ml) was added, maintaining the temperature at <7° C. throughout the addition. A line wash of 2-methyltetrahydrofuran (40 ml) was added. The reaction mixture was warmed to 20° C. and held at 20° C. for 20 minutes. Methanesulphonic acid (66 ml, 1.01 mol) was added over 1 hour and 10 minutes, followed by 2-methyltetrahydrofuran (40 ml). The reaction mixture was stirred at 20° C. over night. Methanesulphonic acid (7 ml, 0.101 mol) was added, followed by 2-methyltetrahydrofuran (7 ml) and the reaction stirred at 20° C. for a further 4 hours. Water (400 ml) was added at room temperature and the resulting biphasic mixture stirred at room temperature for 20 minutes. The lower aqueous layer was removed and a solution of potassium bicarbonate (53.50 g, 0.534 mol) in water (400 ml) was added to the organic layer. The biphasic mixture was stirred at room temperature for 20 minutes and then the lower aqueous solution was removed. The organic fraction was retained (solution of diethyl (3-oxo1,3-dihydro-2-benzofuran-1-yl)phosphonate). 2-Fluoro-5-formylbenzonitrile (64 g, 0.429 mol) was added to the organic fraction and the mixture was stirred at 20° C. Triethylamine (66 ml, 0.473 mol) was added dropwise followed by 2-methyltetrahydrofuran (7 ml). The reaction mixture was stirred at 20° C. over night, then cooled to 5° C., filtered, washed with industrial methylated spirit (480 ml) and then dried in vacuo at up to 40° C. to give the title compound (91.2 g).

Mass Spectrum: MH+266

$^1$H NMR (400 MHz, DMSO-d6) δ: 6.89 (s, 1H, major isomer), 6.94 (s, 1H, minor isomer), 7.40 (dd, 1H, minor isomer), 7.58 (t, 1H, both isomers), 7.70 (t, 1H, both isomers), 7.89 (t, 1H, both isomers), 7.95 (d, 1H, both isomers), 8.05 (d, 1H, both isomers), 8.15 (m, 2H, major isomer).

(b) 2-Fluoro-5-[(4-oxo-3,4-dihydrophthalazin-1-yl)methyl]benzonitrile (ED)

2-Fluoro-5-[(E/Z)-(3-oxo-2-benzofuran-1(3H)-ylidene)methyl]benzonitrile (E)(20 g, 75.40 mmol) and tetrahydrofuran (200 ml) were stirred at room temperature under a nitrogen atmosphere for 30 minutes. Hydrazine monohydrate (4.40 ml, 90.53 mmol) was added, followed by a line wash of tetrahydrofuran (4 ml). The reaction mixture was stirred at room temperature for 1 hour 45 minutes. Acetic acid (1.10 ml, 19.20 mmol) was added and the reaction mixture warmed to 60° C. The reaction mixture was held at 60° C. overnight. The reaction mixture was cooled to 50° C. and water (200 ml) added dropwise. The temperature was maintained at 45° C. throughout the addition. The reaction mixture was cooled to 20° C., filtered, washed with a mixture of water (30 ml) and tetrahydrofuran (30 ml), and then dried in vacuo at up to 40° C. to give the title compound (18.7 g).

Mass spectrum: MH+280

$^1$H NMR (400 MHz, DMSO-d6) δ: 4.38 (s, 2H), 7.46 (t, 1H), 7.72 (m, 1H), 7.85 (dt, 1H), 7.92 (m, 2H), 7.99 (d, 1H), 8.27 (dd, 1H), 12.57 (s, 1H).

(c) 2-Fluoro-5-[(4-oxo-3,4-dihydrophthalazin-1-yl)methyl]benzoic acid (D)

2-Fluoro-5-[(4-oxo-3,4-dihydrophthalazin-1-yl)methyl]benzonitrile (ED) (9.60 g, 34.37 mmol) and water (40 ml) were stirred at 20° C. 2M Sodium hydroxide (36 ml, 72.00 mmol) was added, the reaction mixture warmed to 90° C. and held at this temperature overnight. The reaction mixture was cooled to room temperature and filtered. The filter pad was washed with water (10 ml) and the combined filtrate added to 2M HCl (56 ml, 112.00 mmol) at 60° C. over 40 minutes. The resulting suspension was cooled to 50° C. and filtered, washed with water (57 ml) and dried in vacuo at up to 60° C. to give the title compound as a white solid (9.72 g).

Mass Spectrum: MH+299

$^1$H NMR (400 MHz, DMSO-d6) δ: 4.36 (s, 2H), 7.24 (dd, 1H), 7.59 (m, 1H), 7.84 (dt, 2H), 7.90 (dt, 1H), 7.98 (d, 1H), 8.27 (dd, 1H), 12.59 (s, 1H), 13.22 (brs, 1H).

Example 5

Recrystallisation of Compound A from Aqueous Ethanol 4-(3-{[4-(cyclopropylcarbonyl)piperazin-1-yl]carbonyl}-4-fluorobenzyl)phthalazin-1(2H)-one (compound A) (20.00 g, 44.66 mmol) was suspended in a mixture of water (50 ml) and ethanol (150 ml). The suspension was heated to reflux with stirring. The solution produced was then cooled to 70° C. and filtered. The filter pad was washed with a mixture of water (8 ml) and ethanol (22 ml).

The filtrate was cooled to 45° C. with stirring. 4-(3-{[4-(cyclopropylcarbonyl)piperazin-1-yl]carbonyl}-4-fluorobenzyl)phthalazin-1(2H)-one (Compound A) in Form A (0.08 g) was added in order to seed the mixture. The resulting suspension was cooled to 20° C. over 2.5 hours and was stirred at this temperature for a further 16 hours in order to establish crystallisation. Water (200 ml) was added over 5 hours maintaining the temperature at 20° C. At the end of the addition the suspension was held at 20° C. for 2 hours.

The suspension was filtered and the filter cake washed with a mixture of ethanol (24 ml) and water (56 ml). The isolated solid was discharged and dried under vacuum at 40-60° C., to give the title compound (Form A) as an off white solid (18.1 g).

Figure 3:
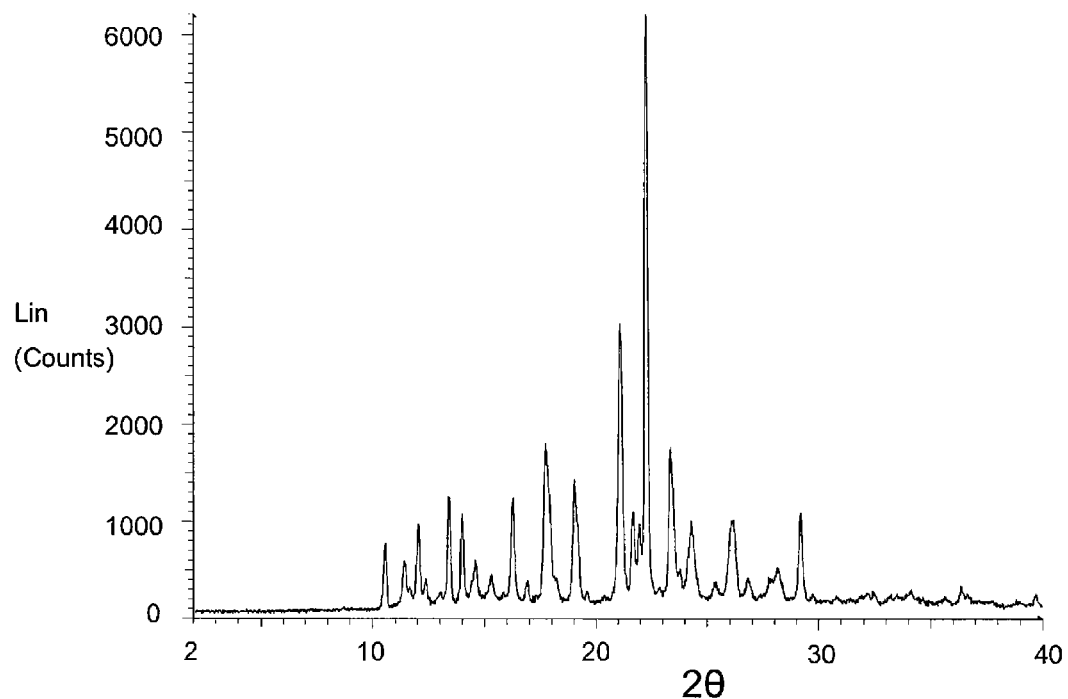
FIG. 3 shows a representative powder XRD pattern of compound A as Form A.

Methods for Obtaining FIGS. 3 of 5

Powder XRD—FIG. 3 (Compound A as Form A)

Powder X-ray diffraction was recorded with a Bruker D5000 diffractometer (wavelength of X-rays 1.5418 Å Cu source, Voltage 40 kV, filament emission 40 mA). Samples were scanned from 2-40° 2θ using a 0.02° step width and a 4 second time count.

Figure 4:
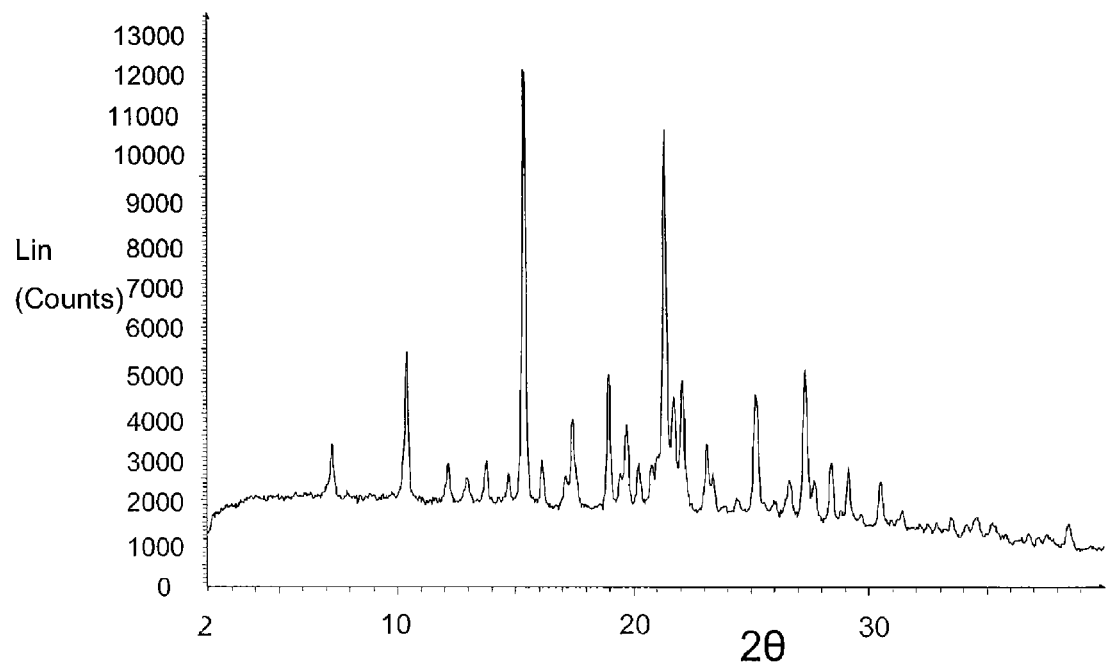
FIG. 4 shows a representative powder XRD pattern of compound A as solvated form.

Powder XRD—FIG. 4 (Compound A as Solvated Form)

Powder X-ray diffraction of the solvate family was recorded with a Inel XRG-3000 diffractometer (wavelength of X-rays 1.5418 Å Cu source, Voltage 40 kV, filament emission 30 mA), fitted with a curved position sensitive detector (range 120°2θ). Samples were scanned from 2.5-40° 2θ using a 0.03° step width typically with a total collection time of 300 s.

Figure 5:
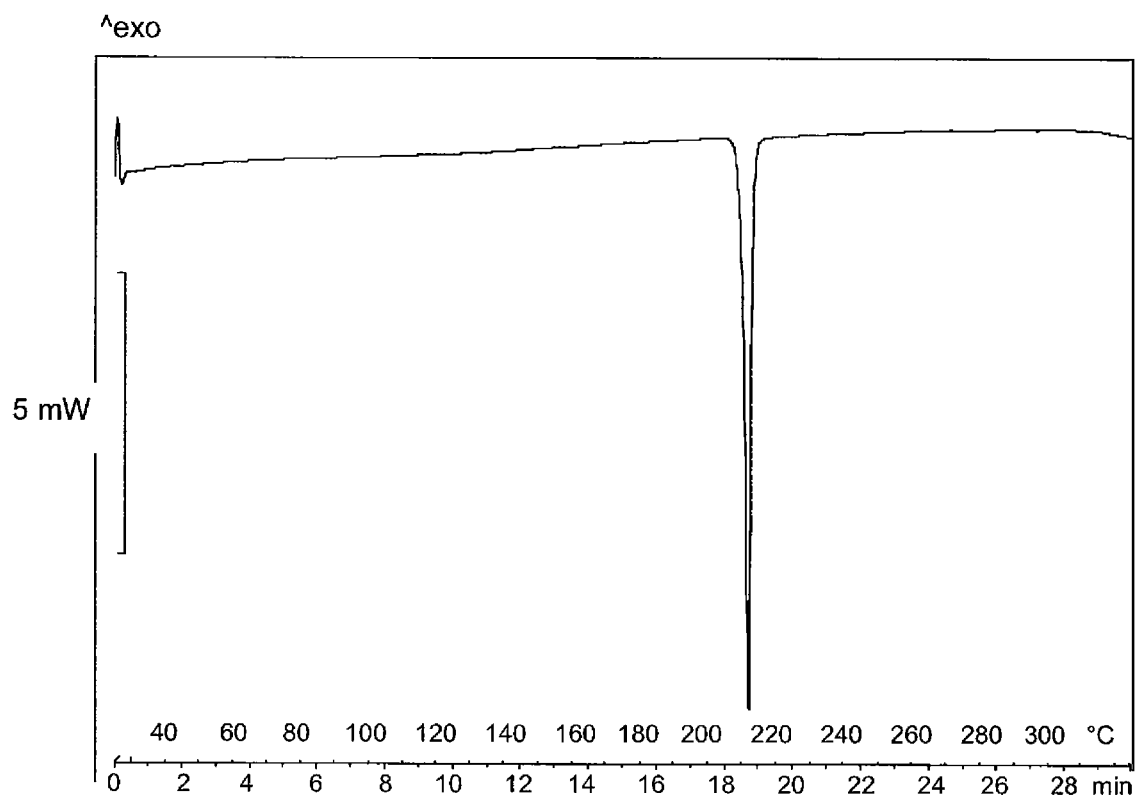
FIG. 5 shows a representative DSC trace of compound A as Form A obtained by heating from 25° C. to 325° C. at 10° C. per minute.

Differential Scanning Calorimetry (DSC)—FIG. 5

DSC was recorded using a Mettler DSC820E with TSO801RO robotic system. Typically less than 5 mg of material, contained in a 40 μl aluminium pan fitted with a pierced lid, was heated over the temperature range 25° C. to 325° C. at a constant heating rate of 10° C. per minute. A nitrogen purge gas was used with flow rate 100 ml per minute.

Example 6

Inhibitory Action

In order to assess the inhibitory action of the active compound, the following assay was used to determine an $IC_{50}$ value.

Mammalian PARP, isolated from Hela cell nuclear extract, was incubated with Z-buffer (25 mM Hepes (Sigma); 12.5 mM MgCl$_2$ (Sigma); 50 mM KCl (Sigma); 1 mM DTT (Sigma); 10% Glycerol (Sigma) 0.001% NP-40 (Sigma); pH 7.4) in 96 well FlashPlates (TRADE MARK) (NEN, UK) and varying concentrations of said inhibitors added. All compounds were diluted in DMSO and gave final assay concentrations of between 10 and 0.01 μM, with the DMSO being at a final concentration of 1% per well. The total assay volume per well was 40 μl.

After 10 minutes incubation at 30° C. the reactions were initiated by the addition of a 10 μl reaction mixture, containing NAD (5 μM), $^3$H-NAD and 30 mer double stranded DNA-oligos. Designated positive and negative reaction wells were done in combination with compound wells (unknowns) in order to calculate % enzyme activities. The plates were then shaken for 2 minutes and incubated at 30° C. for 45 minutes.

Following the incubation, the reactions were quenched by the addition of 50 μl 30% acetic acid to each well. The plates were then shaken for 1 hour at room temperature.

The plates were transferred to a TopCount NXT (TRADE MARK) (Packard, UK) for scintillation counting. Values recorded are counts per minute (cpm) following a 30 second counting of each well.

The % enzyme activity for the compound is then calculated using the following equation:

$$\% \text{ Inhibition} = 100 - \left(100 \times \frac{(cpm \text{ of unknowns} - \text{mean negative } cpm)}{(\text{mean positive } cpm - \text{mean neagative } cpm)}\right)$$

IC$_{50}$ values (the concentration at which 50% of the enzyme activity is inhibited) were calculated, which are determined over a range of different concentrations, normally from 10 μM down to 0.001 μM. Such IC$_{50}$ values are used as comparative values to identify increased compound potencies.

Compound A has an IC$_{50}$ of about 5 nM.

Potentiation Factor

The Potentiation Factor (PF$_{50}$) for the active compound is calculated as a ratio of the IC$_{50}$ of control cell growth divided by the IC$_{50}$ of cell growth+PARP inhibitor. Growth inhibition curves for both control and compound treated cells are in the presence of the alkylating agent methyl methanesulfonate (MMS). The test compound was used at a fixed concentration of 0.2 micromolar. The concentrations of MMS were over a range from 0 to 10 μg/ml.

Cell growth was assessed using the sulforhodamine B (SRB) assay (Skehan, P., et al., (1990) New colorimetric cytotoxicity assay for anticancer-drug screening. J. Natl. Cancer Inst. 82, 1107-1112.). 2,000 HeLa cells were seeded into each well of a flat-bottomed 96-well microtiter plate in a volume of 100 μl and incubated for 6 hours at 37° C. Cells were either replaced with media alone or with media containing PARP inhibitor at a final concentration of 0.5, 1 or 5 μM.

Cells were allowed to grow for a further 1 hour before the addition of MMS at a range of concentrations (typically 0, 1, 2, 3, 5, 7 and 10 μg/ml) to either untreated cells or PARP inhibitor treated cells. Cells treated with PARP inhibitor alone were used to assess the growth inhibition by the PARP inhibitor.

Cells were left for a further 16 hours before replacing the media and allowing the cells to grow for a further 72 hours at 37° C. The media was then removed and the cells fixed with 100 μl of ice cold 10% (w/v) trichloroacetic acid. The plates were incubated at 4° C. for 20 minutes and then washed four times with water. Each well of cells was then stained with 100 μl of 0.4% (w/v) SRB in 1% acetic acid for 20 minutes before washing four times with 1% acetic acid. Plates were then dried for 2 hours at room temperature. The dye from the stained cells was solubilized by the addition of 100 μl of 10 mM Tris Base into each well. Plates were gently shaken and left at room temperature for 30 minutes before measuring the optical density at 564 nM on a Microquant microtiter plate reader.

Compound A has a PF$_{50}$ at 200 nM of at least 20.

The invention claimed is:

1. The compound 4-[3-(4-cyclopropanecarbonyl-piperazine-1-carbonyl)-4-fluoro-benzyl]-2H-phthalazin-1-one as a crystalline form having the following characteristic peaks in a powder X-ray diffraction pattern:

| Peak | 2θ° (±0.1°) λ = 1.5418Å |
|---|---|
| 1 | 12.0 |
| 2 | 17.8 |
| 3 | 21.1 |
| 4 | 22.3 |
| 5 | 29.2. |

2. The compound of claim 1 having the following additional characteristic peaks in a powder X-ray diffraction pattern:

| Peak | 2θ° (±0.1°) (λ = 1.5418Å) |
|---|---|
| 6 | 10.5 |
| 7 | 14.0 |
| 8 | 21.7 |
| 9 | 24.3 |
| 10 | 26.1. |

3. The compound of claim 1, which begins melting at 210.1° C.±1° C. when heated from 25° C. to 325° C. at 10° C. per minute in differential scanning calorimetry.

4. A method of synthesising 4-[3-(4-cyclopropanecarbonyl-piperazine-1-carbonyl)-4-fluoro-benzyl]-2H-phthalazin-1-one from 2-fluoro-5-(4-oxo-3,4-dihydro-phthalazin-1-ylmethyl)-benzoic acid comprising reacting 2-fluoro-5-(4-oxo-3,4-dihydrophthalazin-1-ylmethyl)-benzoic acid with 1-(cyclopropylcarbonyl)piperazine or a mineral acid salt thereof in the presence of an amide coupling agent and a base to form 4-[3-(4-cyclopropanecarbonyl-piperazine-1-carbonyl)-4-fluoro-benzyl]-2H-phthalazin-1-one.

* * * * *